(12) United States Patent
Battrell et al.

(10) Patent No.: US 8,216,832 B2
(45) Date of Patent: Jul. 10, 2012

(54) SANITARY SWAB COLLECTION SYSTEM, MICROFLUIDIC ASSAY DEVICE, AND METHODS FOR DIAGNOSTIC ASSAYS

(75) Inventors: C. Frederick Battrell, Redmond, WA (US); Jason Capodanno, Redmond, WA (US); John Clemmens, Redmond, WA (US); Joan Haab, Seattle, WA (US); John Gerdes, Columbine Valley, CO (US)

(73) Assignee: Micronics, Inc., Redmond, WA (US)

( * ) Notice: Subject to any disclaimer, the term of this patent is extended or adjusted under 35 U.S.C. 154(b) by 69 days.

(21) Appl. No.: 12/695,487

(22) Filed: Jan. 28, 2010

(65) Prior Publication Data

US 2010/0274155 A1 Oct. 28, 2010

Related U.S. Application Data

(63) Continuation of application No. PCT/US2008/071810, filed on Jul. 31, 2008.

(60) Provisional application No. 60/953,045, filed on Jul. 31, 2007.

(51) Int. Cl.
*C12M 1/30* (2006.01)
*C12M 1/26* (2006.01)
*C12M 1/28* (2006.01)

(52) U.S. Cl. ........... 435/309.1; 435/309.2; 435/308.1

(58) Field of Classification Search ............... 435/308.1, 435/309.1, 309.2
See application file for complete search history.

(56) References Cited

U.S. PATENT DOCUMENTS

| | | | |
|---|---|---|---|
| 3,655,503 A | 4/1972 | Stanley et al. | 161/165 |
| 3,691,140 A | 9/1972 | Silver | 260/78.5 |
| 3,915,806 A | 10/1975 | Horlach | 195/139 |
| 4,279,344 A | 7/1981 | Holloway, Jr. | 206/631 |
| 4,683,195 A | 7/1987 | Mullis et al. | 435/6 |
| 4,683,202 A | 7/1987 | Mullis | 435/91 |
| 4,735,837 A | 4/1988 | Miyasaka et al. | 428/40 |
| 4,800,159 A | 1/1989 | Mullis et al. | 435/172.3 |
| 4,803,998 A | 2/1989 | Kezes et al. | 128/759 |
| 5,025,920 A | 6/1991 | Walsh et al. | 206/223 |

(Continued)

FOREIGN PATENT DOCUMENTS

EP 0960825 A2 12/1999

(Continued)

OTHER PUBLICATIONS

Anderson et al., "A miniature integrated device for automated multistep genetic assays," *Nucleic Acids Research* 28(12):e60i-e60vi, Jun. 15, 2000.

(Continued)

*Primary Examiner* — Nathan Bowers
*Assistant Examiner* — Gautam Prakash
(74) *Attorney, Agent, or Firm* — Seed IP Law Group PLLC

(57) ABSTRACT

Biohazard specimen collection containers are provided with an external disposable skin, that is stripped away and discarded after the biohazardous specimen is collected, thus reducing or eliminating objectionable or dangerous residues on the outside surfaces of the container. Further, we teach that the sample collection container with external disposable skin may also serve as an integrated microfluidic biosample processing and analytical device, thereby providing a single entry, disposable assay unit, kit and system for "world-to-result" clinical diagnostic testing. These integrated assay devices are provided with synergic, multiple safe-handling features for protecting healthcare workers who handle them. The modified collection containers and analytical devices find application, for example, in PCR detection of infectious organisms or pathogenic markers collected on a swab.

6 Claims, 14 Drawing Sheets

---

COLLECT A SPECIMEN ON A SWAB;

INSERT THE SWAB TIP INTO COLLECTION DEVICE, THE COLLECTION DEVICE HAVING BEEN PROVIDED WITH DISPOSABLE EXTERNAL SKIN OR SKINS;

BREAK OFF THE SWAB HANDLE, AND SEAL THE SWAB INSIDE THE COLLECTION DEVICE USING A LOCKING, SEALABLE CLOSURE;

REMOVE THE DISPOSABLE SKIN OR SKINS FROM THE EXTERNAL SURFACES OF THE DEVICE, AND DISCARD;

THEN [OPTIONALLY], PERFORM A DIAGNOSTIC ASSAY ON THE CAPTIVE SPECIMEN.

U.S. PATENT DOCUMENTS

| | | | |
|---|---|---|---|
| 5,266,266 A | 11/1993 | Nason | 422/58 |
| 5,296,375 A | 3/1994 | Kricka et al. | 435/291 |
| 5,304,487 A | 4/1994 | Wilding et al. | 435/291 |
| 5,498,392 A | 3/1996 | Wilding et al. | 422/68.1 |
| 5,587,128 A | 12/1996 | Wilding et al. | 422/50 |
| 5,639,423 A | 6/1997 | Northrup et al. | 122/50 |
| 5,726,404 A | 3/1998 | Brody | 200/81 R |
| 5,747,349 A | 5/1998 | van den Engh et al. | 436/172 |
| 5,786,182 A | 7/1998 | Catanzariti et al. | 435/91.1 |
| 5,856,174 A | 1/1999 | Lipshutz et al. | 435/286.5 |
| 5,863,502 A | 1/1999 | Southgate et al. | 422/58 |
| 5,872,710 A | 2/1999 | Kameyama | 363/95 |
| 5,879,635 A | 3/1999 | Nason | 422/102 |
| 5,932,100 A | 8/1999 | Yager et al. | 210/634 |
| 5,939,291 A | 8/1999 | Loewy et al. | 435/91.2 |
| 5,939,312 A | 8/1999 | Baier et al. | 435/287.2 |
| 5,955,029 A | 9/1999 | Wilding et al. | 422/68.1 |
| 5,958,349 A | 9/1999 | Petersen et al. | 422/198 |
| 5,971,158 A | 10/1999 | Yager et al. | 209/155 |
| 6,007,775 A | 12/1999 | Yager | 422/57 |
| 6,054,277 A | 4/2000 | Furcht et al. | 435/6 |
| 6,126,804 A | 10/2000 | Andresen | 204/601 |
| 6,180,372 B1 | 1/2001 | Franzen | 435/91.1 |
| 6,248,294 B1 | 6/2001 | Nason | 422/58 |
| 6,261,431 B1 | 7/2001 | Mathies et al. | 204/601 |
| 6,277,646 B1 | 8/2001 | Guirguis et al. | 436/172 |
| 6,303,343 B1 | 10/2001 | Kopf-Sill | 435/91.1 |
| 6,403,037 B1 | 6/2002 | Chang et al. | 422/68.1 |
| 6,420,143 B1 | 7/2002 | Kopf-Sill | 435/91.1 |
| 6,429,007 B1 | 8/2002 | Kluttz et al. | 435/286.5 |
| 6,431,212 B1 | 8/2002 | Hayenga et al. | 137/855 |
| 6,432,695 B1 | 8/2002 | Zou et al. | 435/287.2 |
| 6,440,725 B1 | 8/2002 | Pourahmadi et al. | 435/288.5 |
| 6,488,896 B2 | 12/2002 | Weigl et al. | 422/101 |
| 6,509,186 B1 | 1/2003 | Zou et al. | 435/286.1 |
| 6,516,947 B1 | 2/2003 | Van Dyke et al. | 206/361 |
| 6,541,213 B1 | 4/2003 | Weigl et al. | 435/7.1 |
| 6,541,274 B2 | 4/2003 | Nagle et al. | 436/180 |
| 6,544,734 B1 | 4/2003 | Briscoe et al. | 435/6 |
| 6,565,808 B2 | 5/2003 | Hudak et al. | 422/58 |
| 6,572,830 B1 | 6/2003 | Burdon et al. | 422/186.29 |
| 6,581,899 B2 | 6/2003 | Williams | 251/7 |
| 6,613,576 B1 | 9/2003 | Rodacy et al. | 436/164 |
| 6,623,821 B1 | 9/2003 | Kendig | 428/34.9 |
| 6,743,399 B1 | 6/2004 | Weigl et al. | 422/102 |
| 6,762,049 B2 | 7/2004 | Zou et al. | 435/287.2 |
| 6,890,484 B2 | 5/2005 | Bautista et al. | 422/58 |
| 6,960,437 B2 | 11/2005 | Enzelberger et al. | 435/6 |
| 6,991,898 B2 | 1/2006 | O'Connor | 435/4 |
| 7,018,830 B2 | 3/2006 | Wilding et al. | 435/287.1 |
| 7,098,040 B2 | 8/2006 | Kaylor et al. | 436/514 |
| 7,223,371 B2 | 5/2007 | Hayenga et al. | 422/100 |
| 7,226,562 B2 | 6/2007 | Holl et al. | 422/68.1 |
| 7,235,607 B2 | 6/2007 | Ohlsson | 525/191 |
| 7,537,730 B2 | 5/2009 | Colin et al. | 422/58 |
| 7,550,267 B2 | 6/2009 | Hawkins et al. | 435/7.1 |
| 7,763,453 B2 | 7/2010 | Clemmens et al. | 435/286.7 |
| 2001/0046701 A1 | 11/2001 | Schulte et al. | 435/287.2 |
| 2002/0160518 A1 | 10/2002 | Hayenga et al. | 436/70 |
| 2002/0187076 A1 | 12/2002 | DiCesare et al. | 422/99 |
| 2003/0124619 A1 | 7/2003 | Weigl et al. | 435/7.1 |
| 2003/0138941 A1 | 7/2003 | Gong et al. | 435/287.2 |
| 2003/0175990 A1 | 9/2003 | Hayenga et al. | 436/164 |
| 2004/0175695 A1 | 9/2004 | Debad et al. | 435/5 |
| 2004/0202571 A1 | 10/2004 | Epler | 422/61 |
| 2005/0009200 A1 | 1/2005 | Guo et al. | 436/174 |
| 2005/0013732 A1 | 1/2005 | Battrell et al. | 422/58 |
| 2005/0084842 A1 | 4/2005 | O'Connor | 435/4 |
| 2005/0106066 A1 | 5/2005 | Saltsman et al. | 422/57 |
| 2005/0129582 A1 | 6/2005 | Breidford et al. | 422/100 |
| 2006/0216196 A1 | 9/2006 | Satoh et al. | 422/61 |
| 2007/0042427 A1 | 2/2007 | Gerdes et al. | 435/7.1 |
| 2009/0061450 A1 | 3/2009 | Hunter | 435/6 |
| 2009/0148933 A1 | 6/2009 | Battrell et al. | 435/287.2 |
| 2009/0181411 A1 | 7/2009 | Battrell et al. | 435/7.92 |
| 2009/0325276 A1 | 12/2009 | Battrell et al. | 435/287.2 |

FOREIGN PATENT DOCUMENTS

| | | |
|---|---|---|
| GB | 2059992 A | 4/1981 |
| WO | WO 94/05414 A1 | 3/1994 |
| WO | WO 97/23596 A1 | 7/1997 |
| WO | WO 97/27324 A1 | 7/1997 |
| WO | WO 98/50147 A1 | 11/1998 |
| WO | WO 01/41931 A2 | 6/2001 |
| WO | WO 02/18823 A1 | 3/2002 |
| WO | WO 03/004162 A1 | 1/2003 |
| WO | WO 2005/032377 A1 | 4/2005 |
| WO | WO 2006/076567 A2 | 7/2006 |
| WO | WO 2007/064635 A1 | 6/2007 |
| WO | WO 2009/018473 A1 | 2/2009 |

OTHER PUBLICATIONS

Ausubel et al., "Current Protocols in Molecular Biology," John Wiley and Sons, Baltimore, MD., 1989.

Belgrader et al., "PCR Detection of Bacteria in Seven Minutes," *Science* 284(5413):449-450, Apr. 16, 1999.

Belgrader et al., "A Battery-Powered Notebook Thermal Cycler for Rapid Multiplex Real-Time PCR Analysis," *Analytical Chemistry* 73(2):286-289, Jan. 15, 2001.

Burke et al., "Microfabrication Technologies for Integrated Nucleic Acid Analysis," *Genome Research* 7:189-197, 1997.

Burns et al., "An Integrated Nanoliter DNA Analysis Device," *Science* 282:484-487, Oct. 16, 1998.

Chartier et al., "Fabrication of an hybrid plastic-silicon microfluidic device for high-throughput Genotyping," *Proceedings of SPIE* 4982:208-219, 2003.

Chiou et al., "A Closed-Cycle Capillary Polymerase Chain Reaction Machine," *Analytical Chemistry* 73(9):2018-2021, May 1, 2001.

Giordano et al., "Polymerase Chain Reaction in Polymeric Microchips: DNA Amplification in Less Than 240 Seconds," *Analytical Biochemistry* 291:124-132, 2001.

Hupert et al., "Polymer-Based Microfluidic Devices for Biomedical Applications," *Proceedings of SPIE* 4982:52-64, 2003.

Innis et al., *PCR Protocols: A Guide to Methods and Applications*, Academic Press, Inc., San Diego, Calif., 1990.

Khandurina et al., "Integrated System for Rapid PCR-Based DNA Analysis in Microfluidic Devices," *Analytical Chemistry* 72(13):2995-3000, Jul. 1, 2000.

Kopp et al., "Chemical Amplification: Continuous-Flow PCR on a Chip," *Science* 280:1046-1048, May 15, 1998.

Lagally et al., "Fully integrated PCR-capillary electrophoresis microsystem for DNA analysis," *Lab on a Chip* 1:102-107, 2001.

Liu et al., "DNA Amplification and Hybridization Assays in Integrated Plastic Monolithic Devices," *Analytical Chemistry* 74(13):3063-3070, Jul. 1, 2002.

Nakano et al., "High Speed Polymerase Chain Reaction in Constant Flow," *Biosci. Biotech. Biochem* 58(2):349-352, Feb. 1994.

Nelson et al., "Self-collected versus provider-collected vaginal swabs for the diagnosis of bacterial vaginosis: An assessment of validity and reliability," *Journal of Clinical Epidemiology* 56:862-866, 2003.

Tüdós et al., "Trends in miniaturized total analysis systems for point-of-care testing in clinical chemistry," *Lab on a Chip* 1:83-95, 2001.

Wilding et al., "PCR in a Silicon Microstructure," *Clinical Chemistry* 40(9):1815-1818, 1994.

Woolley et al., "Functional Integration of PCR Amplification and Capillary Electrophoresis in a Microfabricated DNA Analysis Device," *Analytical Chemistry* 68(23):4081-4086, Dec. 1, 1996.

Yang et al., "High sensitivity PCR assay in plastic micro reactors," *Lab on a Chip* 2:179-187, 2002.

Yuen et al., "Microchip Module for Blood Sample Preparation and Nucleic Acid Amplification Reactions," *Genome Research* 11:405-412, 2001.

Zhang et al., "Miniaturized PCR chips for nucleic acid amplification and analysis: latest advances and future trends," *Nucleic Acids Research* 35(13):4223-4237, 2007.

Zhang et al., "PCR microfluidic devices for DNA amplification," *Biotechnology Advances* 24:243-284, 2006.

Zhou et al., "Determination of SARS-coronavirus by a microfluidic chip system," *Electrophoresis* 25:3032-3039, 2004.

Zou et al., "Micro-assembled multi-chamber thermal cycler for low-cost reaction chip thermal multiplexing," *Sensors and Actuators A* *102*:114-121, 2002.

International Search Report, mailed Jan. 7, 2009, for PCT/US2008/071810, 4 pages.

Written Opinion of the International Searching Authority, mailed Jan. 7, 2009, for PCT/US2008/071810, 6 pages.

International Preliminary Report on Patentability, mailed Jul. 23, 2009, for PCT/US2008/071810, 14 pages.

Fig. 10

COLLECT A SPECIMEN ON A SWAB;

INSERT THE SWAB TIP INTO COLLECTION DEVICE, THE COLLECTION DEVICE HAVING BEEN PROVIDED WITH DISPOSABLE EXTERNAL SKIN OR SKINS;

BREAK OFF THE SWAB HANDLE, AND SEAL THE SWAB INSIDE THE COLLECTION DEVICE USING A LOCKING, SEALABLE CLOSURE;

REMOVE THE DISPOSABLE SKIN OR SKINS FROM THE EXTERNAL SURFACES OF THE DEVICE, AND DISCARD;

THEN [OPTIONALLY], PERFORM A DIAGNOSTIC ASSAY ON THE CAPTIVE SPECIMEN.

Fig. 11

COLLECT A SPECIMEN IN A CONTAINER, THE CONTAINER HAVING DISPOSABLE EXTERNAL SKIN OR SKINS;

SEAL THE ENTRY TO THE CONTAINER WITH A CLOSURE;

REMOVE AND DISCARD THE DISPOSABLE SKIN OR SKINS FROM THE EXTERNAL SURFACES OF THE CONTAINER.

Fig. 15A
Fig. 15B
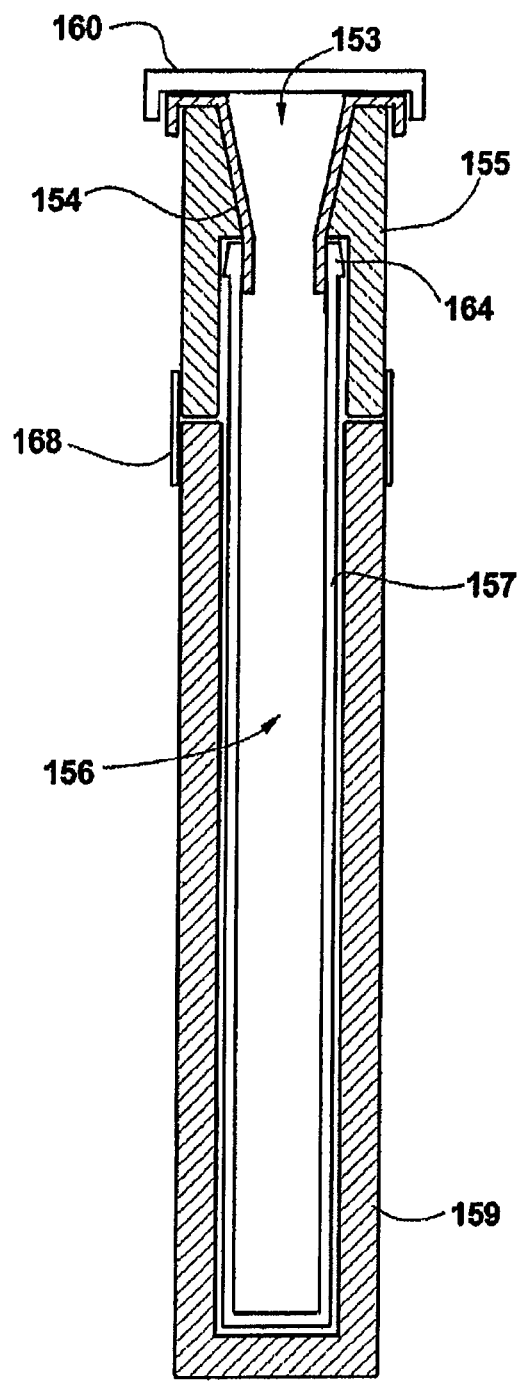
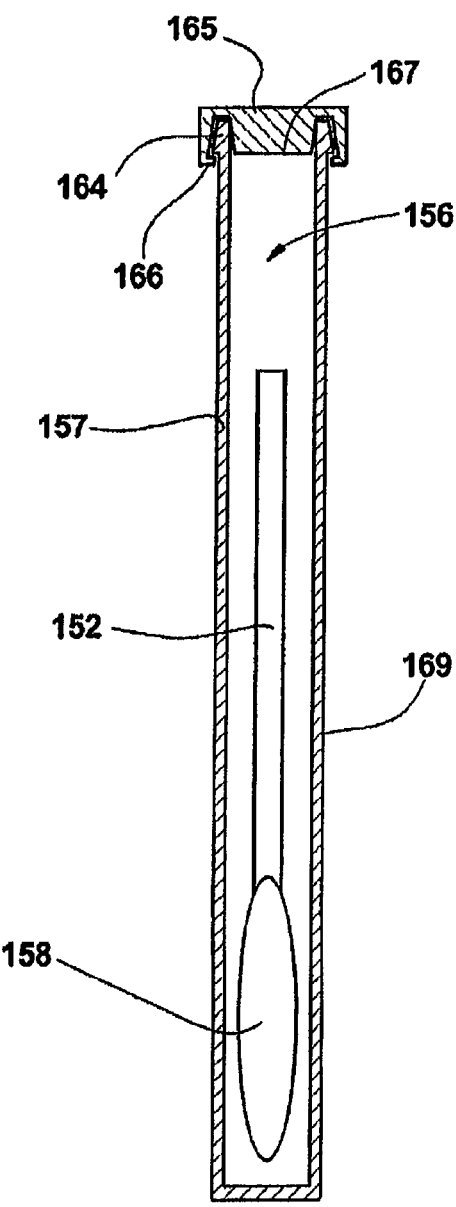

SANITARY SWAB COLLECTION SYSTEM, MICROFLUIDIC ASSAY DEVICE, AND METHODS FOR DIAGNOSTIC ASSAYS

CROSS-REFERENCE TO RELATED APPLICATIONS

This application is a continuation of International PCT Patent Application No. PCT/US2008/071810, filed Jul. 31, 2008, now pending, which claims the benefit under 35 U.S.C. §119(e) of U.S. Provisional Application No. 60/953,045, filed Jul. 31, 2007. The foregoing applications are incorporated herein by reference in their entireties.

STATEMENT OF GOVERNMENT INTEREST

This invention was made with government support under Contract No. U01 AI070801 awarded by National Institutes of Health. The government has certain rights in this invention.

BACKGROUND

1. Technical Field

The invention relates to medical and veterinary sample collection devices and to medical and veterinary analytical devices of specialized form and function, and to integrated microfluidic devices for both sample collection and analysis. The invention further relates to a method for biohazard sample collection.

2. Description of the Related Art

The art relating to handling of swabs is well established, but remains in need of improvement, both to ensure the integrity of the clinical sample and its protection from contamination, but also to ensure that healthcare professionals are not unnecessarily or inadvertently exposed to biological material on the exterior surfaces of the swab container. Once the external surfaces are contaminated during sample collection, exposure readily occurs when a swab container is passed from hand to hand, and no on-board means is known to refresh or cleanse the outside surfaces of the sample container.

We have reviewed the patent literature, and found little or no teaching that comments on this problem. U.S. Pat. No. 4,803,998 to Kezes relates to a swab retaining vial cap and describes a combination containment vial with cap and with swab mounted inside the cap, the vial containing a medium for preserving a sample on the swab during shipment. The swab is removed from the cap to collect a sample and the swab tip can then be broken off when inserted into the vial so that the swab tip drops to the bottom of the vial without contamination by the user. The cap is then sealed. FIG. 4 shows a swab with frangible shaft. The patent is indicative of early efforts to protect a sample from contamination. This seems to accurately reflect the overall state of the art as it exists at this filing. We note that while the interior of the vial is carefully protected from contamination, the exterior is subject to contamination during handling, and becomes a fomite vector for infectious disease. Samples collected in this way are frequently removed for analysis at a separate location, and those who handle the sample container may inadvertently be exposed to material on the exterior surface of the sample container.

U.S. Pat. No. 6,991,898 to O'Connor (Jan. 31, 2006) describes a self-contained diagnostic test device for collection and detection of an analyte in a biological specimen. The device comprises a tubular swab and reagent dispensing cap. The reagent dispensing cap delivers one or more selected reagents to an assay chamber upon the rotation of the reagent chamber.

In U.S. Pat. No. 7,098,040 to Kaylor, a swab-based diagnostic test device is provided. The test device contains a reagent and a rupturable seal for adding the reagent to the sample after the swab is sealed inside the device.

U.S. Pat. No. 6,277,646 to Guirguis provides a device for both collecting and testing a fluid specimen. A fluid specimen is collected and an aliquot is transferred to an isolation chamber, from which a flow path to a test chamber is opened.

U.S. Pat. No. 6,565,808 to Hudak describes a fluid flow actuating device or structure, such as a valve, which separates the sample receiving chamber from the test platform. The test method involves collecting a sample, contacting the sample with the proprietary test device, and detecting the analyte in the sample.

U.S. Pat. No. 6,248,294 to Nason relates to a self-contained diagnostic test unit for use in the collection and analysis of a biological specimen. The test unit comprises is tubular housing for capturing a swab. A reagent dispenser cap delivers reagents to the specimen chamber and a diagnostic strip assembly is mounted on the housing so a portion of the specimen can flow by wick action through the test strip, producing a visible color change.

U.S. Pat. Nos. 5,266,266 and 5,879,635 to Nason relate to a reagent dispenser which includes a pair of reagent chambers with selected reagents therein, and a dual nib for hermetically sealing the reagent chambers. A portion of the dispenser is deformable to break or otherwise to displace the nib in a manner permitting the two reagents to flow together and mix within one of the reagent chambers. The deformable portion or the dispenser can then be squeezed to express the mixed reagents for delivery to contact the specimen to be analyzed. In a preferred form, the dispenser is a cap assembly on an open-ended tubular housing configured for receiving a swab.

Similarly, U.S. Pat. No. 6,890,484 to Bautista relates to in-line test device and describes a swab receiving port integrated into the body of a lateral flow strip. No means for protecting the exterior of the test apparatus is described. Goodfield, in Sampling and Assay Device (WO1997/23596), discloses a swab and swab container with liquid assay reagents accessible by rupture of foil liners, again with no outer disposable protective layer.

All the above devices and methods are deficient for the present purpose in that the operator is exposed to contamination of the external surfaces of the specimen collection container by contact with residues of specimen or unrelated patient-derived bodily material, which may be unhygienic and grossly objectionable. This problem is apparently not considered.

United States Patent Application 2005/0009200 to Guo relates to a sanitary and compact fecal occult blood collector kit. The swab tip in this case is covered "for hygienic purposes". Also disclosed is a package for the swab and the cover. However, on closer study, the purpose of the cover is again to protect the sample, not the handle of the swab contacted by the operator or the external surfaces of the swab collection container, and the exterior of the package cannot be cleaned of contaminating matter that accumulates during sampling. Further, the swab must again be retrieved from the package. Thus while the sample is protected, the user is potentially exposed at multiple levels.

Miniaturizing some of the processes involved in clinical analyses, including nucleic acid, immunological and enzymatic analysis, or combinations thereof, has been achieved using microfluidic devices. Microfluidic techniques known in the art include electrophoretic detectors, for example those designed by ACLARA BIOSCIENCES® Inc., or the LAB-CHIP®™ by Caliper Technologies Inc, and hybridization detectors such as those manufactured by Nanogen of San Diego. Also indicative of the state of the art are PCT Publication WO1994/05414, U.S.Pat. Nos. 5,498,392, 5,304,487, 5,296,375, 5,856,174, 6,180,372, 5,939,312, 5,939,291, 5,863,502, 6,054,277, 6,261,431, 6,440,725, 5,587,128, 5,955,029, 5,498,392, 5,639,423, 5,786,182, 6,261,431, 6,126,804, 5,958,349, 6,303,343, 6,403,037, 6,429,007, 6,420,143, 6,572,830, 6,541,274, 6,544,734, 6,960,437, 6,762,049, 6,509,186, 6,432,695, 7,018,830, and 2001/0046701, 2003/0138941, and International Pat. Nos. WO 2003/004162, WO2002/18823, WO2001/041931, WO1998/50147, WO1997/27324, all of which describe apparatuses and methods incorporating various microfluidic processing and analytical operations involved in nucleic acid analysis, and are incorporated herein by reference.

Co-assigned to MICRONICS®, Inc of Redmond WA, and also incorporated herein in full by reference, are U.S. Patent No. 6,743,399 ("Pumpless Microfluidics"), U.S. Patent No. 6,488,896 ("Microfluidic Analysis Cartridge"), U.S. Patent No. 5,726,404 ("Valveless Liquid Microswitch"), U.S. Patent No. 5,932,100 ("Microfabricated Differential Extraction Device and Method"), ("Tangential Flow Planar Microfluidic Fluid Filter"), U.S. Patent No. 5,872,710 ("Microfabricated Diffusion-Based Chemical Sensor"), U.S. Patent No. 5,971,158 ("Absorption-Enhancing Differential Extraction Device"), U.S. Patent No. 6,007,775 ("Multiple Analyte Diffusion-Based Chemical Sensor"), U.S. Patent No. 6,581,899 ("Valve for Use in Microfluidic Structures"), U.S. Patent No. 6,431,212 ("Valve for Use in Microfluidic Structures"), U.S. Patent No. 7,223,371 ("Microfluidic Channel Network Device"), U.S. Patent No. 6,541,213 ("Microscale Diffusion Immunoassay"), U.S. Patent No. 7,226,562 ("Liquid Analysis Cartridge"), U.S. Patent No. 5,747,349 ("Fluorescent Reporter Beads for Fluid Analysis"), US Patent Applications 2005/0106066 ("Microfluidic Devices for Fluid Manipulation and Analysis"), 2002/0160518 ("Microfluidic Sedimentation"), 2003/0124619 ("Microscale Diffusion Immunoassay"), 2003/0175990 ("Microfluidic Channel Network Device"), 2005/0013732 ("Method and system for Microfluidic Manipulation, Amplification and Analysis of Fluids"), 2007/0042427, "Microfluidic Laminar Flow Detection Strip", 2005/0129582 (System and Method for Heating, Cooling and Heat Cycling on a Microfluidic Device); and unpublished US Patent documents titled, "Integrated Nucleic Acid Assays," "Microfluidic Cell Capture and Mixing Circuit", "Microfluidic Mixing and Analytical Apparatus," "System and Method for Diagnosis of Infectious Diseases", "Methods and Devices for Microfluidic Point of Care Assays", "Integrated Microfluidic Assay Devices and Methods", and "Microscale Diffusion Immunoassay Utilizing Multivalent Reactants", all of which are hereby incorporated in full by reference. Also representative of microfluidic technologies that are co-assigned to MICRONICS® are PCT Publications WO 2006/076567 and 2007/064635, all incorporated herein in full by reference for what they enable.

The utility and breadth of microfluidic assays for nucleic acid assays is further demonstrated in the scientific literature, the teachings of which are incorporated by reference herein. These teachings include, for example, Nakano H et al. 1994. High speed polymerase chain reaction in constant flow. Biosci Biotechnol Biochem 58:349-52; Wilding, P et al. 1994. PCR in a silicon microstructure. Clin Chem 40(9):1815-18; Woolley A T et al. 1996. Functional integration of PCR amplification and capillary electrophoresis in a microfabricated DNA analysis device. Anal Chem 68:4081-86; Burke D T et al. 1997. Microfabrication technologies for integrated nucleic acid analysis. Genome Res 7:189-197; Kopp et al. 1998. Chemical amplification: continuous-flow PCR on a chip. Science 280:1046-48; Burns, M A. 1998. An Integrated Nanoliter DNA Analysis Device. Science 282:484-87; Belgrader P et al. 1999. PCR Detection of bacteria in seven minutes. Science 284:449-50; Lagally E T et al. 2001. Fully integrated PCR-capillary electrophoresis microsystem for DNA analysis. Lab Chip 1:102-07; Tudos A J et al. 2001. Trends in miniaturized total analysis systems for point-of-care testing in clinical chemistry. Lab Chip 1:83-95; Belgrader P et al. 2002. A battery-powered notebook thermocycler for rapid multiplex real-time PCR analysis. Anal Chem 73:286-89; Hupert L M et al. 2003. Polymer-Based Microfluidic Devices for Biomedical Applications. In, (H Becker and P Woias, eds) Microfluidics, BioMEMS, and Medical Microsystems, Proc SPIE Vol 4982:52-64; Chartier I et al. 2003. Fabrication of an hybrid plastic-silicon microfluidic device for high-throughput genotyping. In, (H Becker and P Woias, eds) Microfluidics, BioMEMS, and Medical Microsystems, Proc SPIE Vol 4982:208-219; Anderson R C et al. 2000. A miniature integrated device for automated multistep genetic assays. Nucl Acids Res 28(12):[e60, i-vi]; Yang, J et al. 2002. High sensitivity PCR assay in plastic micro reactors. Lab Chip 2:179-87; Giordano B C et al. 2001. Polymerase chain reaction in polymeric microchips: DNA amplification in less than 240 sec. Anal Biochem 291:124-132; Khandurina J et al. 2000. Integrated system for rapid PCR-based DNA analysis in microfluidic devices. Anal Chem 72:2995-3000; Chiou, J et al. 2001. A Closed-Cycle Capillary Polymerase Chain Reaction Machine. Anal Chem 73:2018-21; Yuen, P K et al. 2001. Microchip module for blood sample preparation and nucleic acid amplification reactions. Genome Res 11:405-412; Zhou X, et al. 2004. Determination of SARS-coronavirus by a microfluidic chip system. Electrophoresis. 25(17):3032-9; Liu Y et al. 2002. DNA amplification and hybridization assays in integrated plastic monolithic devices. Anal Chem 74(13):3063-70; Zou, Q et al. 2002. Micro-assembled multi-chamber thermal cycler for low-cost reaction chip thermal multiplexing. Sensors Actuators A 102:224-121; Zhang C et al. 2006. PCR Microfluidic devices for DNA amplification. Biotech Adv 24:243-84, and Zhang, C and Xing D. 2007. Miniaturized PCR chips for nucleic acid amplification and analysis: latest advances and future trends. Nucl Acids Res 35(13):4223-37.

Thus there is a clear and ongoing interest in microfluidic devices for clinical and veterinary diagnostic assays. As these commercial applications increase, the world-to-chip interface is receiving increasing attention, and we note that little has been done in the area of sample collection to both improve the validity of nucleic acid amplifications by preventing cross-sample contamination, and just as importantly, to prevent exposure of those persons handling the specimens to objectionable or potentially infectious materials. As has been noted, (Nelson, D. B. et al. 2003. "Self-Collected Versus Provider-Collected Vaginal Swabs for the Diagnosis of Bacterial Vaginosis: an Assessment of Validity and Reliability," J Clin Epidemiol, 56:862-866), there is an increasing trend toward patient self-collection of samples, often with swabs or cups. Typically the patient is not provided with means to ensure that the external surfaces of the sample collection device does not become contaminated with the sample or related biological fluids during handling. These swabs or cups are typically then processed or handled by ungloved couriers and paraprofessionals and must then be transferred to the analytical device or further handled and processed by nursing and laboratory personnel. The sample collection device thus becomes a fomite potentially capable of spreading infectious disease to numerous persons, and a method or means for eliminating or at least reducing the exposure of health workers to the contaminated exterior of the sample collection vials, bottles, cups, tubes, and so forth, has been a longstanding and unmet need in the healthcare industry.

Furthermore, awareness of the dangers of unsafe handing of biological fluids and specimens has increased dramatically in the last two decades, and single-entry devices are increasingly needed that seamlessly integrate sample preparation, extraction, and analysis without unnecessary operator exposure. A further objective we have identified is the need to fully integrate the device into a disposable format, so that once a sample is collected, either by patient or by a health professional, all remaining steps of the analysis, up to and including display of the result, are performed without further personal exposure to the sample. A critical step in this process is thus the refreshing or disinfecting of the external surface sample collection container (whether it is also the analytical device or not), and to our knowledge, satisfactory solutions to this problem have not been recognized or brought forward prior to our disclosure herein.

BRIEF SUMMARY

Swabs are extremely useful for collecting specimens. Following collection of a specimen on a swab, the swab must be generally protected during subsequent transport and processing for analysis. During initial handling, contamination of the external surfaces of the swab collection container by contact with residues of specimen or unrelated patient-derived bodily material, which may be unhygienic and grossly objectionable, is almost inevitable. Gloves are protective only to the hands on which they are worn, not to the swab collection container. We see a solution to this problem as an unrecognized and unmet need with significant potential benefits, particularly in reduction of nosocomial infections, for example, and more generally in reduction of disease transmission to health care workers, and also in improvement of sample quality, which is mandatory for tests such as PCR, where false positives due to cross-contamination will invalidate any testing system.

Cross-contamination by transmission on the surfaces of fomites is a longstanding problem. We find that this problem can be alleviated or significantly reduced by applying a disposable external skin to the collection device, and by removing the skin after the risk of exposure to further contamination is ended. Contamination risk is most great during the act of specimen collection itself, and decreases greatly after the specimen collection container is removed from the sampling site. Contamination of the external surfaces of an article passed from hand-to-hand, or hand-to-machine, with normal flora and normal squamous epithelial cells, is significantly less likely to result in false diagnostic positives for a pathogenic condition.

We disclose a biohazard swab collection device or container, comprising a body with external surfaces, an internal hollow volume, and a sealable closure for separating said external surfaces from said internal hollow volume, said external surface further comprising a disposable external skin layer, whereby after the biohazardous swab is enclosed and sealed within the internal hollow volume, any biohazardous residues accumulated on the external surfaces are removed by removing and disposing of the disposable external skin layer, and further optionally comprising a valve separating said internal hollow volume into a swab receiving chamber and a microfluidic assay circuit with a microfluidic channel and an on-board liquid reagent.

We further disclose a method wherein the specimen is not limited to a swab and the specimen collection device is not limited to an analytical device. The general method comprises the steps of:

a) providing a sample and a specimen collection container with body and with sample receiving orifice, said body with external surface and internal hollow volume, said external surface with disposable skin or skins, said sample receiving orifice with sealable closure;

b) inserting said sample into said sample receiving orifice;

c) closing said sealable closure said sample receiving orifice; thereby capturing said sample; and, d) removing said disposable skin or skins from said external surface; thereby renewing said external surface.

BRIEF DESCRIPTION OF THE FIGURES

FIG. 10 is a block diagram of the steps of a method for collecting a biohazardous swab in a swab collection device fitted with a disposable external sanitary skin.

FIG. 11 is a block diagram of the more general steps of a method for collecting a biohazardous specimen in a specimen collection device fitted with a disposable external sanitary skin.

FIGS. 15A and B is a first embodiment of a specimen collection device for a swab where the specimen collection device has no analytical capacity.

DETAILED DESCRIPTION

Definitions

Figure 1:
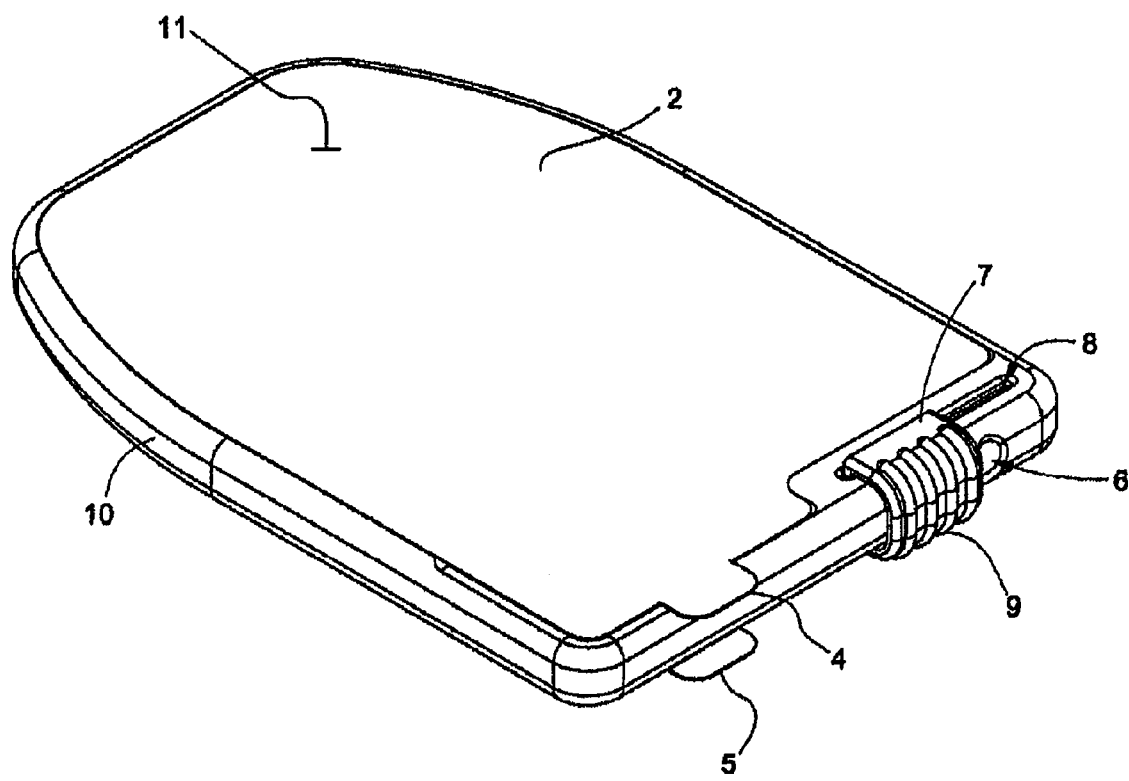
FIG. 1 is a perspective view of a representative specimen collection device with external skins and with integrated sample processing and analytical assay capability.

The following definitions are provided as an aid in interpreting the claims and specification herein. Where works are cited or incorporated by reference, and any definition contained therein is inconsistent with that supplied here, the definition used therein shall not supersede or limit the definition supplied herein.

Fomite: An inanimate object or substance, such as a doorknob, utensil, soap bar, or specimen container, that is capable of transmitting infectious organisms (broadly bacterial and viral) from one individual to another, typically by hand-to-hand or hand-to-mouth exposure to a biological residue on the surface of the inanimate object or substance.

Test samples: Representative biosamples taken by swab include, for example: gingival, buccal, and mucosal epithelial materials, saliva, wound exudates, pus, surgical specimens, lung and other respiratory secretions, nasal secretions, sinus drainage, sputum, blood, urine, medial and inner ear contents, ocular secretions and mucosa, cyst contents, cerebral spinal fluid, stool, diarrhoeal fluid, tears, mammary secretions, ovarian contents, ascites fluid, mucous, gastric fluid, gastrointestinal contents, urethral discharge, vaginal discharge, vaginal mucosa, synovial fluid, peritoneal fluid, meconium, amniotic fluid, semen, penile discharge, or the like may be presented for testing on a swab. Assay from swabs representative of mucosal secretions and epithelia are acceptable, for example mucosal swabs of the throat, tonsils, gingival, nasal passages, vagina, urethra, rectum, lower colon, and eyes. Besides physiological fluids, samples of water, industrial discharges, food products, milk, air filtrates, and so forth are also likely test specimens. Particularly preferred as samples are biosamples collected on swabs or tampons, where a tampon is essentially a handleless swab that is sometimes worn internally before testing.

Biohazard: A biohazard is a material, either biologically active or inanimate, that poses a risk or threat to health. Also included in this category as biohazards, sensu lato, as defined here, are materials of likely biological origin that are visually, tangibly, or odorously objectionable or repulsive, and those materials which are not in fact a threat, but which potentially are a threat until tested negative. Biohazards include potentially infectious material of any kind, and may contain infectious agents from multiple biological categories, including but limited to, bacteria and viruses, either singly or in one or more combinations thereof, and microbial products such as toxins.

Bioassay Target Molecule: or "analyte of interest", or "target molecule", may include a nucleic acid, a protein, an antigen, an antibody, a carbohydrate, a cell component, a lipid, a receptor ligand, a small molecule such as a drug, and so forth. Target nucleic acids include genes, portions of genes, regulatory sequences of genes, mRNAs, rRNAs, tRNAs, siRNAs, cDNA and may be single stranded, double stranded or triple stranded. Some nucleic acid targets have polymorphisms, deletions and alternate splice sequences. Multiple target domains may exist in a single molecule, for example an immunogen may include multiple antigenic determinants. An antibody includes variable regions, constant regions, and the Fc region, which is of value in immobilizing antibodies. The microfluidic analytical devices of the present invention are configured to detect a bioassay target molecule of these sorts, singly or in combinations.

Such bioassay target molecules may be associated with a pathogenic condition: which is taken as a condition of a mammalian host characterized by the absence of health, i.e., a disease, infirmity, morbidity, or a genetic trait associated with potential morbidity.

Microfluidic cartridge: a "device", "card", or "chip" with fluidic structures and internal channels having microfluidic dimensions. These fluidic structures may include chambers, valves, vents, vias, pumps, inlets, nipples, and detection means, for example. Generally, microfluidic channels are fluid passages having at least one internal cross-sectional dimension that is less than about 500 µm and typically between about 0.1 µm and about 500 µm, but we extend the upper limit of the range to 600 um because the macroscopic character of the bead suspensions sometimes used as analytical aids require it. Therefore, as defined herein, microfluidic channels are fluid passages having at least one internal cross-sectional dimension that is less than 600 um.

Microfluidic cartridges may be fabricated from various materials using techniques such as laser stenciling, embossing, stamping, injection molding, masking, etching, and three-dimensional soft lithography. Laminated microfluidic cartridges are further fabricated with adhesive interlayers or by adhesiveless bonding techniques, such by thermal or pressure treatment of oriented polypropylene or by ultrasonic welding. The microarchitecture of laminated and molded microfluidic cartridges can differ according to the limitations of their fabrication methods.

Microfluidic pumps: include for example, bulbs, bellows, diaphragms, or bubbles intended to force movement of fluids, where the substructures of the pump have a thicknesses or other dimension of less than 1 millimeter. Such pumps include the mechanically actuated recirculating pumps described in U.S. Pat. No. 6,743,399 to Weigl and US 2005/0106066 to Saltsman, commonly assigned to the applicant. Such pumps may be robotically operated or operated by hand. Electroosmotic pumps are also provided. Such pumps can be used in place of external drives to propulse the flow of solubilized reagents and sample in microfluidic device-based assays.

Blister pack: an on-board reagent pack or sachet under a deformable (or elastic) diaphragm. Used to deliver reagents by pressurizing the diaphragm and may appose a "sharp", such as a metal chevron, so that pressure on the diaphragm ruptures the "pillow" (see pillow). These may be used with check valves or closable vents to produce directional fluid flow and reagent delivery. Elastic diaphragms are readily obtained from polyurethane, polysilicone and polybutadiene, and nitrile for example (see elastomer). Deformable, inelastic diaphragms are made with polyethylene terephthalate (PET), MYLAR® (Biaxially-oriented polyethylene terephthalate), polypropylene, polycarbonate, or nylon, for example. Other suitable materials for the deformable film include PARAFILM® (i.e., paraffin film), latex, foil, and polyethylene terephthalate Key factors in selecting a deformable film include the yield point and the deformation relaxation coefficient (elastic modulus).

Use of these devices permits delivery or acceptance of a fluid while isolating the contents of the microfluidic device from the external environment, and protecting the user from exposure to the fluid contents.

Single entry: refers to a microfluidic device, card or cartridge that requires, or permits, only a single introduction of sample, and the assay is then conducted within a self-contained, sealed system. Such devices optionally contain a device for sealing or locking the sample port and an on-board means for disinfecting the contents of the device and any waste following completion of the assay. In one embodiment, the device can be discarded after use without special precautions.

Waste chamber or "pack": is a cavity or chamber that serves as a receptacle for sequestering discharged sample, rinse solution, and waste reagents. Typically also includes a wicking material (see wick). Waste packs may also be sealed under an elastic isolation membrane sealingly attached to the body of the microfluidic device. This inner membrane expands as the bibulous material expands, thus enclosing the waste material. The cavity outside the isolation membrane is vented to atmosphere so that the waste material is contained and isolated. Waste packs may optionally contain dried or liquid sterilants.

Vent: a pore intercommunicating between an internal cavity and the atmosphere. A "sanitary" or "isolation vent" also contains a filter element that is permeable to gas, but is hydrophobic and resists wetting. Optionally these filter elements have pore diameters of 0.45 microns or less. These filters function both in forward and reverse isolation. Filter elements of this type and construction may also be placed internally, for example to isolate a valve or bellows pump from the pneumatic manifold controlling it.

Herein, where a "means for a function" is described, it should be understood that the scope of the invention is not limited to the mode or modes illustrated in the drawings alone, but also encompasses all means for performing the function that are described in this specification, and all other means commonly known in the art at the time of filing. A "prior art means" encompasses all means for performing the function as are known to one skilled in the art at the time of filing, including the cumulative knowledge in the art cited herein by reference to a few examples.

Means for extracting: refers to various cited elements of a device, such as a solid substrate, filter, filter plug, bead bed, frit, or column, for capturing target nucleic acids from a biological sample, and includes the cumulative knowledge in the art cited herein. Extracting further comprises methods of solubilizing, and relates to the resuspension of cells and tissue from the tip of a swab. This includes methods, for example, for dissolution of mucous and protein as described in United States Patent Application 2004/0175695 to Debad. Generally, extraction means include a mechanical pumping component that promotes physical resuspension by turbulent or near turbulent flow. Such flow may be reciprocating flow, and may be pulsatile at varying frequencies to achieve the desired resuspension in a reasonable interval of time. Extraction means also include use of detergent-based buffers, sulfhydryl-reducing agents, proteolytics, chaotropes, passivators, and other solubilizing means.

A means for polymerizing, for example, may refer to various species of molecular machinery described as polymerases and their cofactors and substrates, for example reverse transcriptases and TAQ polymerase, and includes the cumulative knowledge of enzymology cited herein by reference to a few examples.

Means for Amplifying: The grandfather of this art is the "polymerase chain reaction" (referred to as PCR) which is described in detail in U.S. Pat. Nos. 4,683,195, 4,683,202 and 4,800,159, Ausubel et al. Current Protocols in Molecular Biology, John Wiley and Sons, Baltimore, Md. (1989), and in Innis et al., ("PCR Protocols", Academic Press, Inc., San Diego Calif., 1990). Polymerase chain reaction methodologies require thermocycling and are well known in the art. Briefly, in PCR, two primer sequences are prepared that are complementary to regions on opposite complementary strands of a target sequence. An excess of deoxynucleoside triphosphates are added to a reaction mixture along with a DNA polymerase, e.g., Taq polymerase. If the target sequence is present in a sample, the primers will bind to the target and the polymerase will cause the primers to be extended along the marker sequence by adding on nucleotides. By raising and lowering the temperature of the reaction mixture, the extended primers will dissociate from the template to form reaction products, excess primers will bind to the template and to the reaction products and the process is repeated. By adding fluorescent intercalating agents, PCR products can be detected in real time.

Other amplification protocols include LAMP (loop-mediated isothermal amplification of DNA) reverse transcription polymerase chain reaction (RT-PCR), ligase chain reaction ("LCR"), transcription-based amplification systems (TAS), including nucleic acid sequence based amplification (NASBA), "Rolling Circle", "RACE" and "one-sided PCR".

These various non-PCR amplification protocols have various advantages in diagnostic assays, but PCR remains the workhorse in the molecular biology laboratory and in clinical diagnostics. Embodiments disclosed here for microfluidic PCR should be considered representative and exemplary of a general class of microfluidic devices capable of executing one or various amplification protocols.

Means for detecting: as used herein, refers to an apparatus for displaying an endpoint, i.e., the result of an assay, and may include a detection channel and test pads, and a means for evaluation of a detection endpoint. Detection endpoints are evaluated by an observer visually in a test field, or by a machine equipped with a spectrophotometer, fluorometer, luminometer, photomultiplier tube, photodiode, nephlometer, photon counter, voltmeter, ammeter, pH meter, capacitative sensor, radio-frequency transmitter, magnetoresistometer, or Hall-effect device. Magnetic particles, beads and microspheres haing or impregnated color or having a higher diffraction index may be used to facilitate visual or machine-enhanced detection of an assay endpoint. Magnifying lenses in the cover plate, optical filters, colored fluids and labeling may be used to improve detection and interpretation of assay results. Means for detection of magnetic particles, beads and microspheres may also include embedded or coated "labels" or "tags" such as, but not limited to, dyes such as chromophores and fluorophores; radio frequency tags, plasmon resonance, spintronic, radiolabel, Raman scattering, chemoluminescence, or inductive moment as are known in the prior art. Colloidal particles with unique chromogenic signatures depending on their self-association are also anticipated to provide detectable endpoints. QDots, such as CdSe coated with ZnS, decorated on magnetic beads, or amalgamations of QDots and paramagnetic $Fe_3O_4$ microparticles, optionally in a sol gel microparticulate matrix or prepared in a reverse emulsion, are a convenient method of improving the sensitivity of an assay of the present invention, thereby permitting smaller test pads and larger arrays. Fluorescence quenching detection endpoints are also anticipated. A variety of substrate and product chromophores associated with enzyme-linked immunoassays are also well known in the art and provide a means for amplifying a detection signal so as to improve the sensitivity of the assay, for example "up-converting" fluorophores. Detection systems are optionally qualitative, quantitative or semi-quantitative. Visual detection is preferred for its simplicity, however detection means can involve visual detection, machine detection, manual detection or automated detection.

Means for isolation include impermeable cartridge body, gas permeable hydrophobic venting, bibulous padding in waste chamber, disinfectant in waste chamber, elastomeric membrane separating pneumatic actuator from blister pack, valve with elastomeric membrane actuated by suction pressure, suction pressure in said sample entry port, on-board reagent pack, self-locking single-entry sample port, gasketed closure, and disposable external skin or skins. Isolation refers both to the protection of the user from potentially biohazardous specimens, and to the protection of the specimen from contamination by the user or by foreign environmental materials. Closure means, or "means for sealingly closing", include caps, lids, threaded closures, "ziplock" closures, ball valves, gasketed closures, gaskets, seals, snap caps of all sorts, bungs, corks, stoppers, lip seals, press seals, adhesive seals, waterproof seals, single-entry seals, tamper-proof seals, locking seals, track-slidable sealable covers, compression seals, one-way valves, spring-loaded valves, spring-loaded lids, septa, tee-valves, snap-locking closures in general, piston-valves, double-reed valves, diaphragm closures, hinged closures, folding closures, Luer lock closures, and so forth.

Unless the context requires otherwise, throughout the specification and claims which follow, the word "comprise" and variations thereof, such as, "comprises" and "comprising" are to be construed in an open, inclusive sense, that is, as "including, but not limited to".

"Conventional" is a term designating that which is known in the prior art to which this invention relates.

"About" and "generally" are broadening expressions of inexactitude, describing a condition of being "more or less", "approximately", or "almost" in the sense of "just about", where variation would be insignificant, obvious, or of equivalent utility or function, and further indicating the existence of obvious minor exceptions to a norm, rule or limit.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Turning now to the figures, FIG. 1 is a conceptual view of a microfluidic analytical device (1) with integrated sanitary swab collection features. The device, which is hand sized, is provided with upper and lower disposable external skins (2, lower not shown). Tabs (4,5) assist in peeling off the skins. These skins are removed after the specimen collection process is completed. Also shown is the swab receiving orifice (6) and sliding closure (7) in the open position for receiving a swab. The closure is provided with a seal and track guide (8) whereby the closure is slid into position sealingly covering the swab receiving orifice. The closure is textured with ribs (9) to aid the thumb in moving from left to right (as shown here) in order to effectuate swab capture within the device. The card body (10) is bounded by external surfaces (11).

Figure 2:
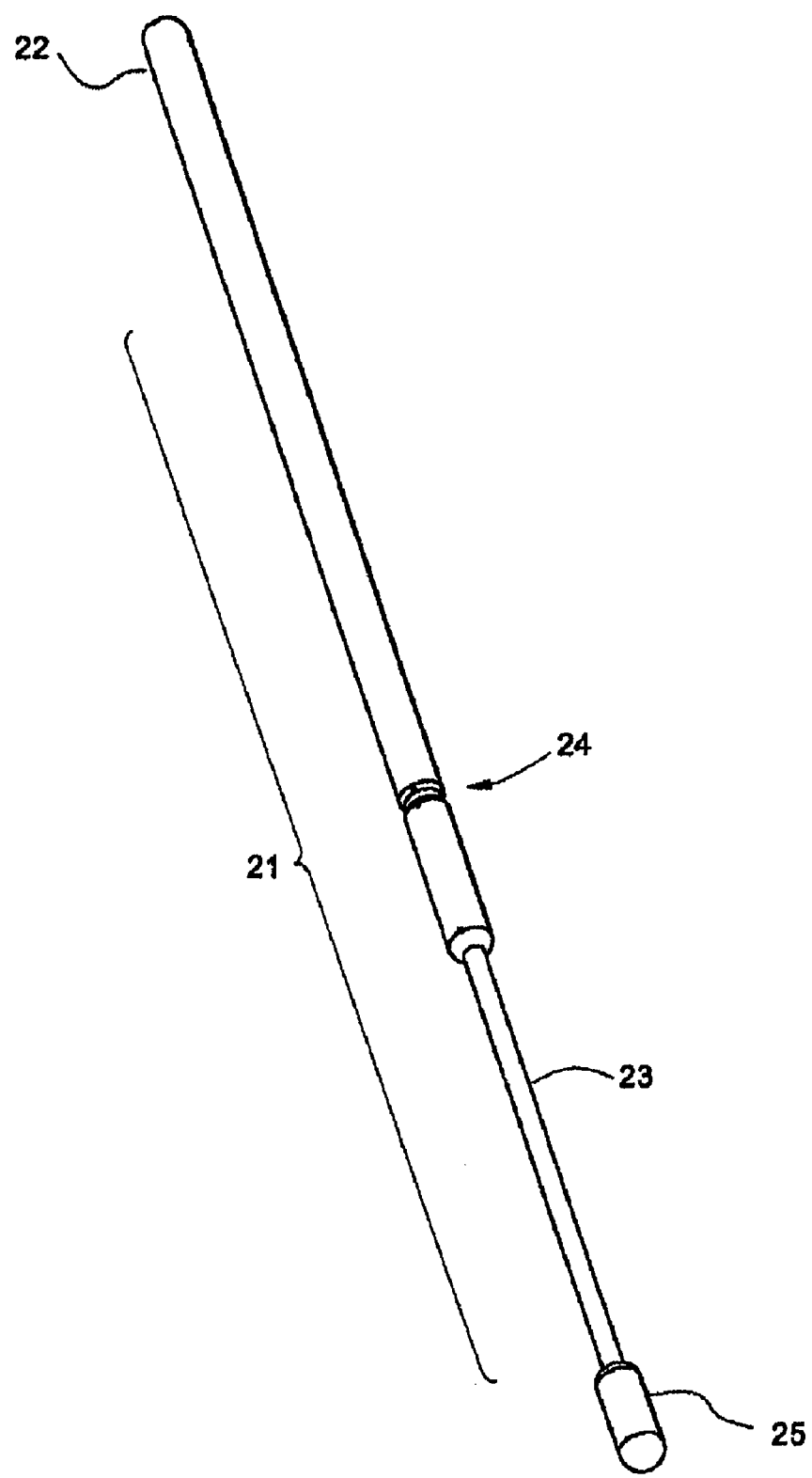
FIG. 2 is a perspective view of a sample swab with frangible handle.

FIG. 2 is a representation of a swab (20) as would be used in an embodiment of the invention. The swab comprises a shaft (21) with handle portion (22), neck portion (23), frangible breakaway notch (24), and tip (25) mounted at the distal end of the shaft. The shaft may be of various shapes or materials. Shaft materials include polypropylene, polyurethane, polycarbonate, polyethylene terephthalate, and other polyesters. Also conceived are polyimides such as nylon and natural fibers such as pine, bamboo, compressed paper, and so forth.

The tip may be of various shapes or materials. Preferred swab shapes include a pipe-cleaner shape of bristles, a spade shape with sponge pad, and a "bud" shape with fiber bat. Non-limiting examples of synthetic fiber materials useful in forming swabs include acetate fibers, aramide fibers, polyamide fibers, e.g. nylons, polyester fibers, e.g. polyethylene terephthalate fibers (PET), polyolefin fibers, e.g. polypropylene and polyethylene fibers, polyvinyl alcohol fibers, polyurethane fibers or foams, and mixtures thereof. Further suitable synthetic fibers include bi- or tricomponent fibers such as PE/PET- or PP/PE fibers. These fibers can for example be so-called core-sheath-, side-by-side- or island-in-the-sea type fibers, as may be useful in selected applications. Lyocell fibers are also useful. Non-synthetic materials include woven paper or cotton. Fiber chemistry is generally chosen to be compatible with extraction or analytical chemistries.

Swab fibers may be interlaid, either knitted or randomly entwined. Interlaid webs or fabrics have been formed from many processes, such as, for example, meltblowing processes, spunbonding processes, and bonded carded web processes. In particular embodiments, interlaid swab materials as utilized in the present invention are produced from polymers, such as, for example, polyethylene or polypropylene. The swab fibers optionally may be made from interbonded fibers, for example as of thermoplastic fibers. The term "fibers" as used herein refers to a broad range of thermoplastic members that can be used to form a nonwoven fabric, including members having defined lengths like staple fibers, meltblown fibers that show a beginning and an end, filaments having endless or continuous lengths, and the like. For example, and without limiting the generality of the foregoing, thermoplastic polymers such as polyolefins including polyethylene, polypropylene as well as polystyrene can be used as may be polyesters including polyethylene terephthalate, and polyamides including nylons. Also useful are other thermoplastic polymers such as those which are elastomeric including elastomeric polyurethanes and block copolymers. Compatible blends of any of the foregoing may also be used. In addition, additives such as wax, fillers, and the like may be incorporated in amounts consistent with the fiber forming process used to achieve desired results. Other fiber or filament forming materials will suggest themselves to those skilled in the art. Bicomponent fibers may be also used. The fibers may also be formed from solution, and examples include viscose. It is only essential that the composition be capable of spinning into filaments or fibers of some form that can be deposited onto a forming surface and thermally formed or interbonded in a manner dependent upon the forming surface. The swab tip may comprise a sponge element.

Figure 3A:
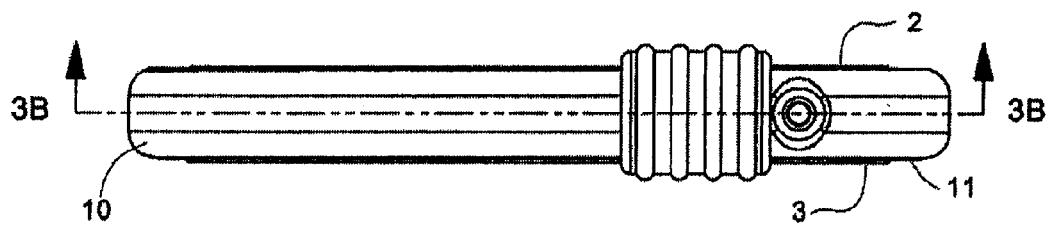
FIG. 3A is a plan view of the upper surface of the device of FIG. 1, and shows section plane 3B.

FIG. 3 shows a representative device for swab capture and analysis. FIG. 3A is a plan view of the top surface of the device, showing plane of section 3B and the location of the swab receiving orifice and sealing closure. In FIG. 3A, the device body 10 and exterior surfaces 11 are again shown.

Figure 3B:
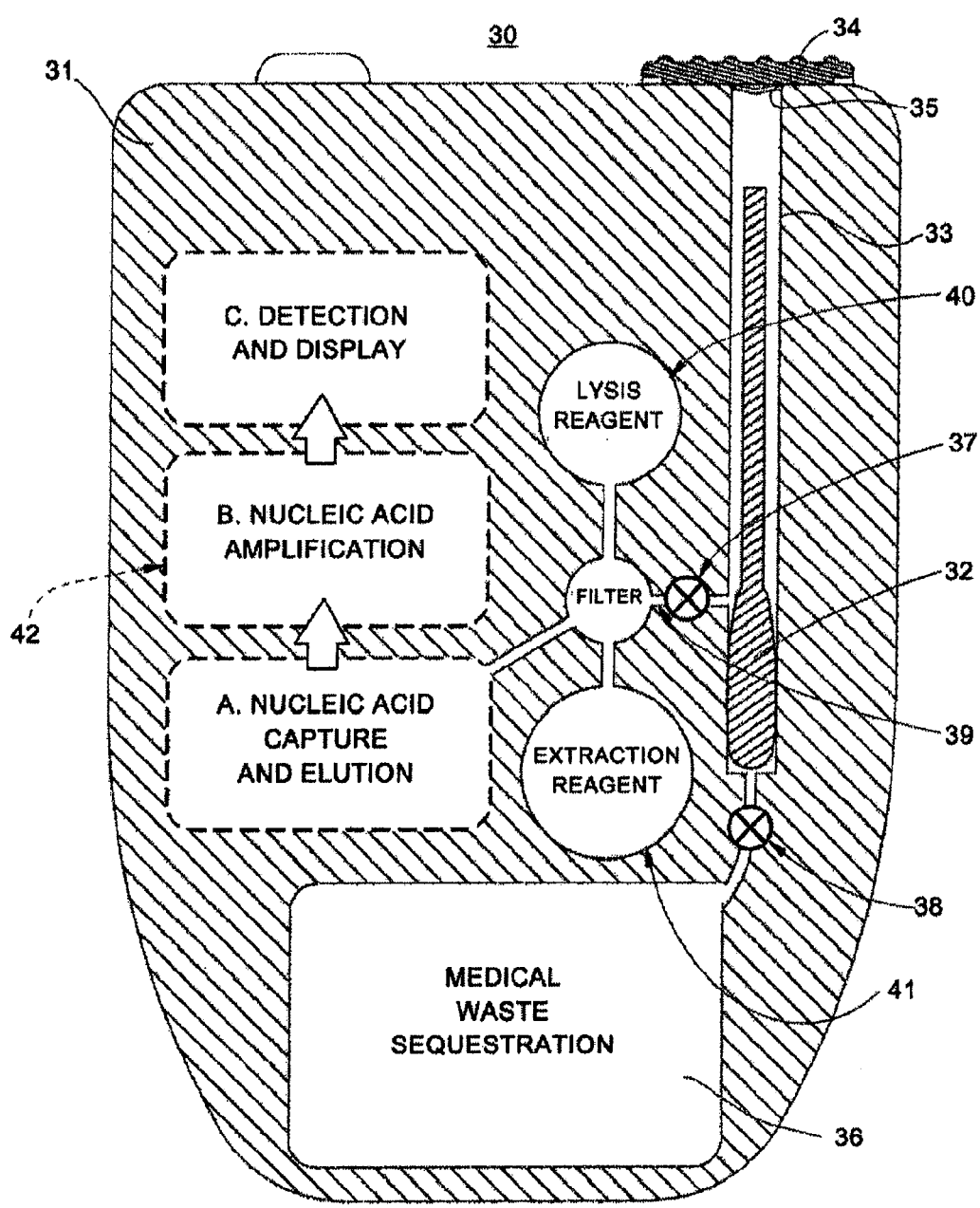
FIG. 3B is a section of the device of FIG. 1 on plane 3B, and shows the swab receiving chamber and inner workings of an embodiment of the integrated device. Representative inner workings are indicated schematically.

FIG. 3B is a view of the internal workings of a representative device (30), showing a section through the device solid body interior (31), with captive swab tip (32) in swab receiving chamber (33), also termed herein an "internal hollow volume". In this view, closure (34) and gasket (35) form a liquid-tight seal over the swab receiving chamber 33. Also shown in schematic form are the elements of an on-board nucleic acid assay. Generally, at least one valve (37) will separate the internal hollow volume of the device body into at least two compartments, one for the sample receiving chamber and the other the analytical microfluidics compartment or circuit (dotted lines with arrows, 42). Other valves (38) may also be used to add functionality to the microfluidic circuit. Any valve known in the art may be used. On-board microfluidic elements for a nucleic acid assay include at least one microfluidic channel (39), and optionally provision for reagent packs such as for lysis reagent and extract reagents (40,41), and an optional microfluidic nucleic acid assay circuit (42), shown schematically. In this embodiment, the internal hollow volume comprises a first compartment for receiving the swab (33) and a second compartment (42, dotted lines) for performing a fluidic operation on the sample, such as a sample preparation step or a sample analysis such as PCR. Generally, the first and second compartments are joined by a valved (37) microfluidic channel (39). This channel provides for fluidic connection between the compartments so that reagent and sample may be interchanged. Other compartments such as waste compartment (36) may also be provided. Variants of the illustrated microfluidic circuit for joining the compartments and exchanging fluids between the compartments are readily within the scope of the invention. Sample processing steps could include extraction of the biological material and lysis of cells of interest, followed by filtration and entry of the filtrate into a nucleic acid capture and elution module. Steps of capture, elution, amplification and detection are indicated without detail. Mesoscale devices for amplification and detection of a nucleic acid in a sample were first described in 1992 (U.S. Pat. No. 5,498,392 to Wilding, "Mesoscale Polynucleotide Amplification Device and Method") and conventional mechanisms are known to those skilled in the art. These devices include various filters, pumps, vents, microfluidic channels, valves, and so forth. The device also optionally includes a display capability, although this function could be a simple visual indicator, or could be a complex interaction between the device and a docking site on an instrument that examines fluorescence of an array or a lateral flow strip, and so forth. Therefore, both stand-alone manual diagnostic applications and automated or semi-automated applications are envisaged. The inner workings of these devices are defined in various embodiments of the prior art. It should be noted that the claimed invention is not limited to a particular embodiment of the inner workings, and that applications for devices used in performing chemical or immunoassays are also anticipated. Devices may be built to assay for bioassay target molecules indicative of pathological conditions and biological threats of any kind.

Sealing closure 34 comprises a gasket or gasket layer 35. In this embodiment, the guide track 8 serves also to force a tight seal between the gasket material and the swab receiving orifice 6, thus forming a fluid-tight seal over swab capture chamber 33. Following capture, the swab is treated by flowing extraction reagent or buffer in and out of the swab receiving chamber. The extraction buffer may include detergents, solvents such as water, and water in combination with DMSO, NMP, DMF, Formamide, THF, and detergents, co-detergents, cosolvents, proteolytics, sulfhydryl-reducing agents such as n-acetyl-cysteine and dithiothreitol, selective nucleases, mucopolysaccharidases, cellulases, proteases, and the like. A discussion of mucolytics is provided in United States Patent Application 2004/0175695 to Debad. Mechanical agitation is important, and may be enhanced by sonication, such as with piezoelectric transducers. For reciprocal flow, air in the chamber can be vented through the waste sequestration chamber or at a secondary vent site. Optionally, the swab receiving chamber may contain active pump elements in tandem pairs, operating in alternation by positive and negative displacement, so that venting is not required. The structure of these paired pump elements consists of elastomeric or flexible diaphragms and the operation requires merely that as the diaphragm of one pump element is compressed, the other diaphragm is distended, so that the fluid is forced back and forth between the two pump elements. The diaphragms may be operated manually, hydraulically, electrostatically, magnetically, or pneumatically as is known in the art.

An important capacity of any such device is the sequestration of medical waste. The device will typically contain buffer and bioactive reagents for sample processing and analysis and all such material is best viewed as biohazardous. Ideally, all such waste is retained in the sealed body of the device and can be disposed of without hazard by autoclaving or incinerating the device itself. Shown here is a waste chamber (36) that would in operation be vented. Such vents as are permeable to air but not to liquid are well known. Added isolation is possible using a flexible diaphragm as described in co-assigned US Patent Document "Integrated Nucleic Acid Assays", where fully operative details of assay systems of this sort are disclosed, and which is herein incorporated in full by reference. Also useful are absorbent bats.

Preferably, the devices are self-contained and contain at least on-board reagent for conducting the analysis. In some cases the reagent is a fluid, for example an extraction buffer or a lysis reagent, but in other cases the reagent is a dried biological, for example a primer mix, an antibody, a polymerase, a divalent cation, or a dried weak acid and its salt. By designing the device to be self-contained, single entry use at the point-of-care is enabled. Liquid reagent storage may be achieved by supplying the reagents in sachets, which are ruptured when needed, by methods known in the art. These methods typically supply a sharp upon which the sachet is compressed so that it ruptures. Compression of the sachet may be by manual means or by pneumatic means.

Figure 4:
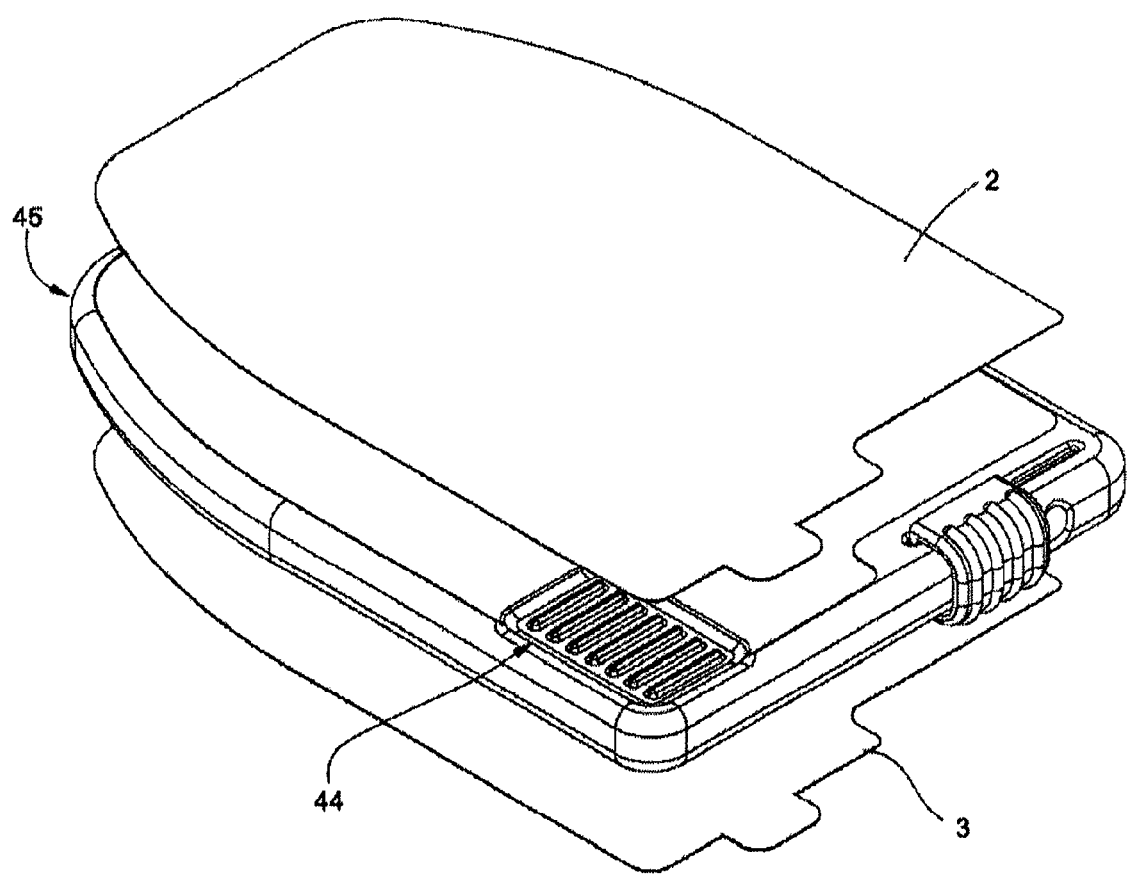
FIG. 4 is an exploded view of protective external disposable skins applied to a representative specimen collection device.

FIG. 4 shows an exploded view of disposable external skins (2,3) applied to a device body (45). Here, both the upper skin (2) and lower skin (3) are shown. A ribbed surface (44) is provided for gripping the device. These skins may be applied as decals. The upper and lower skins may be made from a flexible plastic film or sheet, such as polyethylene, vinyl, polyvinyl chloride, PET or polyurethane, and are typically applied to the device with a removable, pressure sensitive adhesive that can be removed without residue. Candidate commercially available films include 3M™ SCOTCHCAL™ Graphic Film Series 3470 or -3M™ SCOTCHCAL™ Graphic Film Series 8000 available from 3M (St. Paul. MN) and adhesives include ROBOND™ PS-8211 latexes available from Rohm And Haas (Philadephia, PA). Other suitable decal materials include paper sheet, waxed paper sheet, and fiber/plastic or plastic/plastic composite sheets or films, such as polyethylene film bonded over cloth scrim. These sheets or films are typically printed with graphics and written instructions for the user. Optionally the instructions are printed onto the device body and the film cover is transparent. The adhesive is typically an acrylate derivative. Examples of repositionable and removable adhesives are emulsified polymers made from "soft" monomers such as n-butyl acrylate, isooctyl acrylate, or the like, or ionomeric copolymers made from a soft component, such as isobutylene, n-butyl acrylate, isooctyl acrylate, ethyl hexyl acrylate, or the like; in combination with a polar monomer such as acrylic acid, acrylonitrile, acrylamide, methacrylic acid, methyl methacrylate, trimethylamine methacrylimide, trimethylamine p-vinyl benzimide, ammonium acrylate, sodium acrylate, N,N-dimethyl-N-(.beta.-methacryloxyethyl) ammonium propionate betaine, 1,1-dimethyl-1-(2-hydroxypropyl) amine methacrylimide, 4,4,9-trimethyl-4-Azonia -7-oxo-8-oxa-9- decene-1- sulphonate, 1,1-dimethyl-1-(2,3-dihydroxypropyl) amine methacrylimide, and maleic anhydride or the like. Non-spherical polyacrylate adhesives are commercially available, for example, as the Rohm and Haas RHOPLEX™ line of adhesives. The adhesive applied to the film is typically repositionable or removable without residue, the adhesive may be selected from any adhesive that may be repeatably adhered to and removed from a substrate without substantial loss of adhesion capability. An example of such an adhesive is disclosed in U.S. Pat. No. 3,691,140 to Silver, which relates to solid tacky microspheres. Preferred adhesives are water resistant when dry. Repositionable adhesives are also known in which microspheres contained in the adhesive are non-tacky. A disclosure of this type of adhesive is provided in U.S. Pat. No. 4,735,837 to Miyasaka, which describes removable adhesives containing elastic micro-balls with the desired properties. The decal to be applied to the device is typically supplied on a release liner and has good moisture and chemical resistance and the adhesive has a working life of greater than 6 months. The decal may be a composite multilayered sheet to achieve these objectives. Multilayered decals variously fabricated from overlayer, liquid crystalline polymer, plastic, silicone, rubber, thermoplastic, paper, interlaid fiber, underlayer, microporous plastic, backing, scrim, cloth, and adhesive are anticipated for this use.

Figure 5:
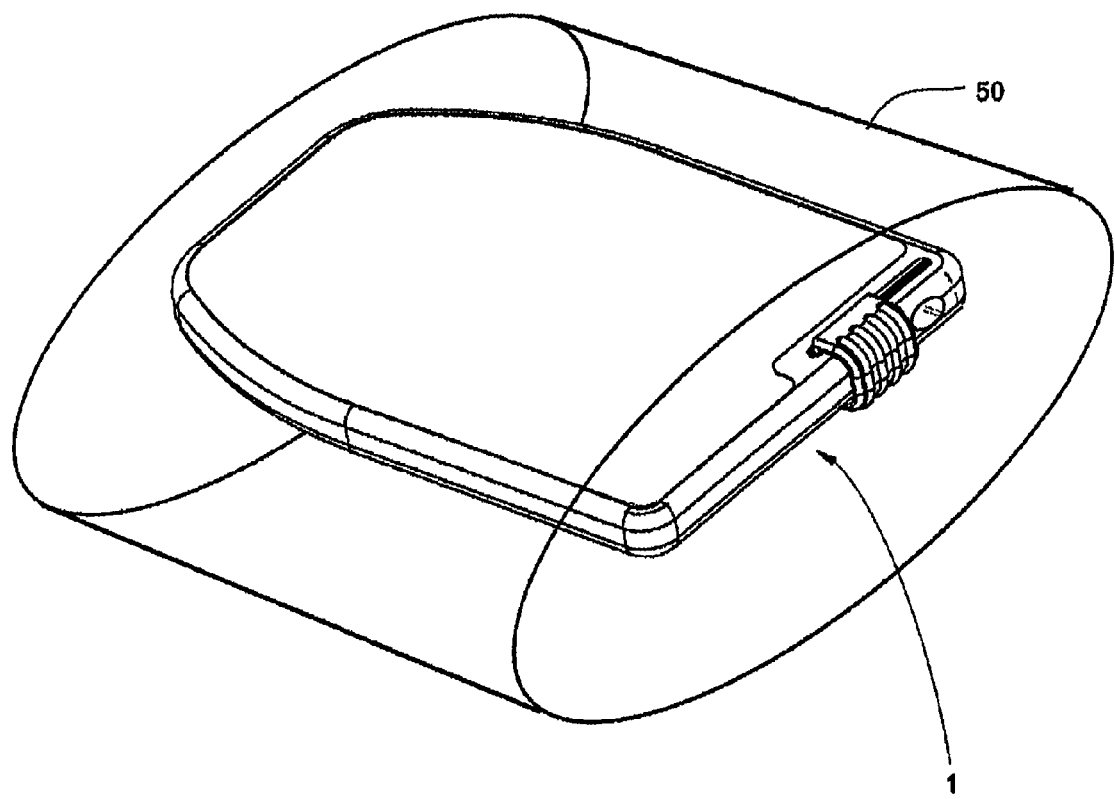
FIG. 5 is a conceptual illustration of the manufacture of a heat-shrink external disposable skin on a representative specimen collection device.

FIG. 5 shows a representation of how a disposable protective cover can be applied using tubestock of heatshrink plastic (50), as is readily commercially available. Once the device is inside a suitable length of the heatshrink material, heat is applied to form the coverlayer to the shape of the device. The swab receiving orifice can be provided with an adhesive-backed decal or appliqué that would be removed immediately before use, exposing the orifice, and also serves as a tamper-evident seal. A tearstrip may similarly be applied to the heatshrink wrapping so that the entire skin can be removed with a single motion. Candidate heat shrinkable thermoplastic films include those polyethylene composites described in U.S. Pat. No. 7,235,607, the polyethylene terephthalate esters of U.S. Pat. No. 6,623,821, and the thermoplastics of U.S. Pat. No. 3,655,503, for example.

Figure 6:
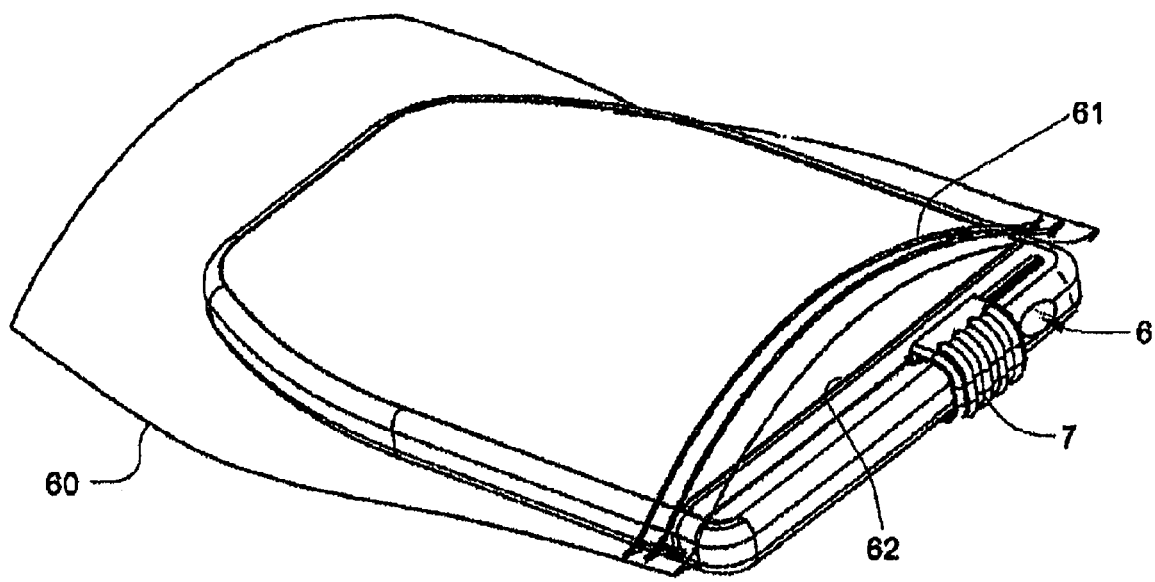
FIG. 6 is an illustration of the assembly of a disposable bag applied to a representative specimen collection device.

FIG. 6 describes a similar protective cover, but made out of a soft plastic bag such as a polyethylene or polyolefin, or out of paper. The paper may be impregnated with a water repellent material or may be absorbent. The plastic or paper bag (60) is formed to include a male sealing rib (61) that mates with a corresponding female locking groove (62) on the exterior circumference of the device body. A tearstrip is provided for ease of removal. The swab receiving orifice 6 can be configured to a variety of swab dimensions and shapes. When the swab is safely captured within the device, closure 7 is pushed across the opening to seal the device.

Figure 7:
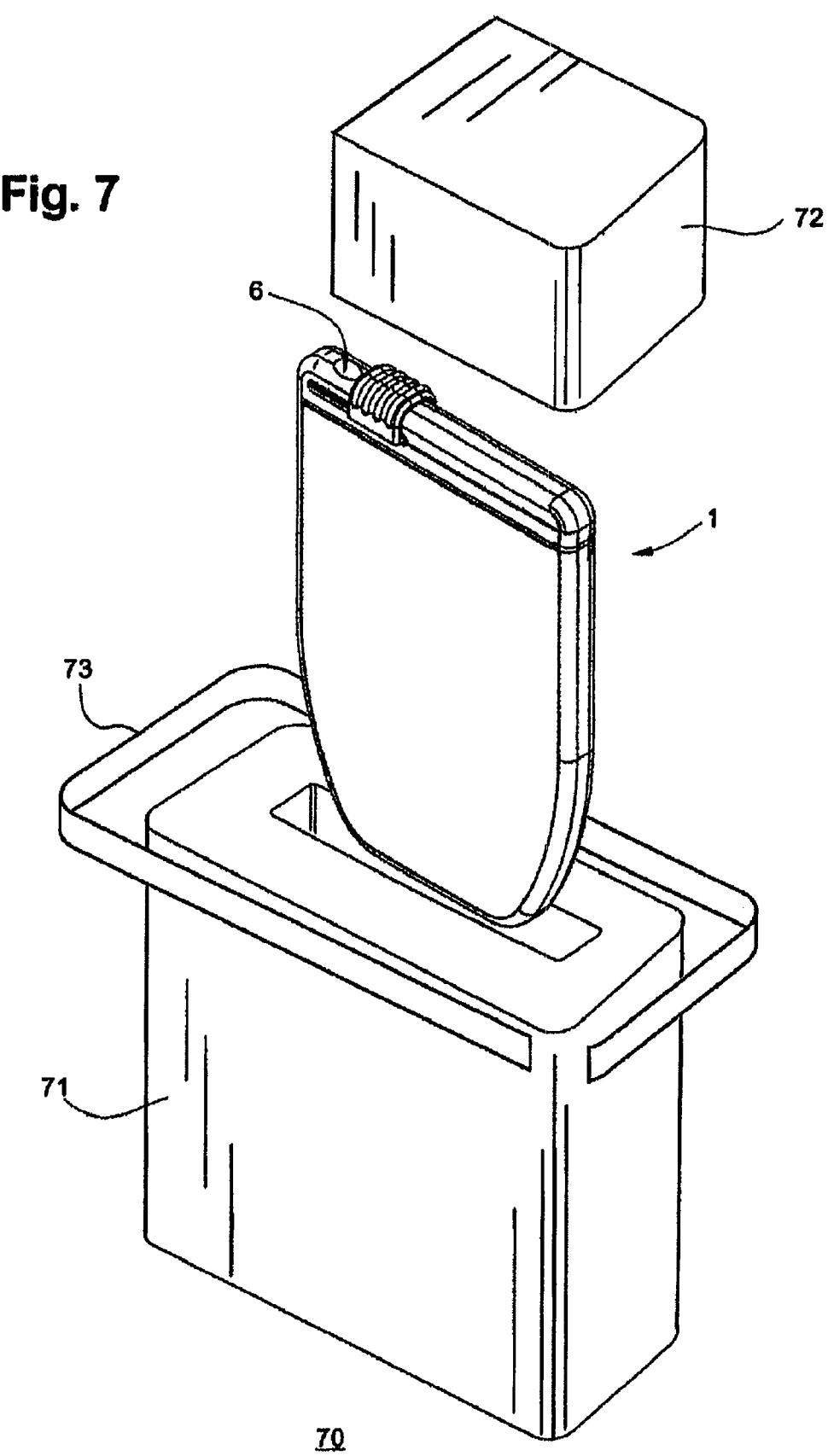
FIG. 7 is an exploded view of a Styrofoam or composite coverblock assembly applied to a representative specimen collection device.

The theme is repeated in the composite device (70) of FIG. 7. Here the disposable outer skin consists of a Styrofoam block or similar expanded material formed by molding, which is fabricated to fit the lower half of the device (71), and a partial lid fitted to the upper half of the device (72), leaving the swab receiving orifice 6 exposed. A tearstrip (73) serves the dual function of adhering the two halves of the outer skin together during sample collection, and is then torn or peeled away so that the halves can be separated and the device removed for further processing or analysis. The tearstrip typically includes a freehanging tab to facilitate this. The lower block and upper lid are discarded after the device is removed.

Note that the shape of the blocks forming the outer skin 70 is variable. A clamshell formed of right and left halves is equally suitable, as are more complex interdigitated two part blocks. A single block is useful. The dual block system has the advantage that squeezing pressure applied to the lower block has the effect of holding the device in place while the tear strip and upper lid are removed. The device can then be pulled out of the lower block with clean hands and presents an uncontaminated exterior, the closure having been pulled over the swab receiving orifice from its protected position under the upper lid.

Figure 8:
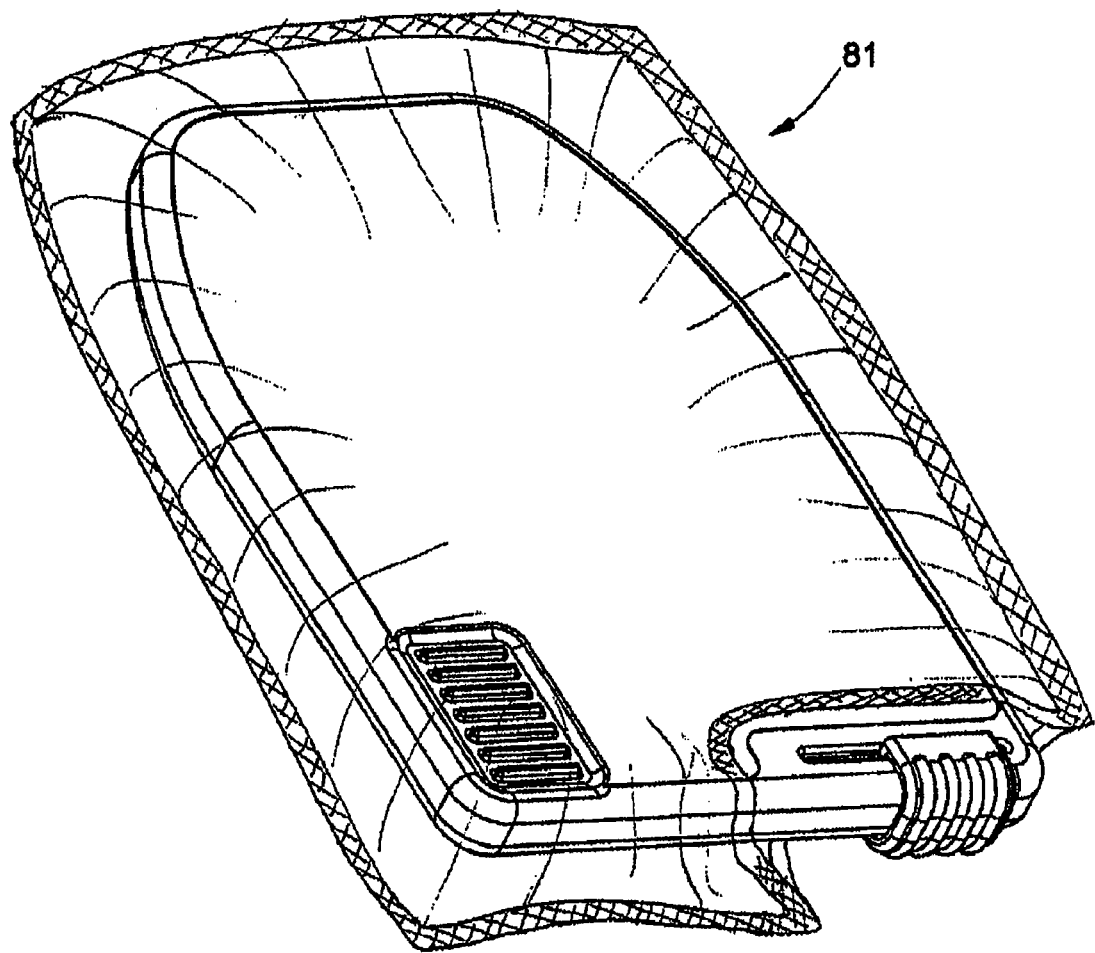
FIG. 8 is a sketch of a device with composite cover formed in place over and around the device.
Figure 9A:
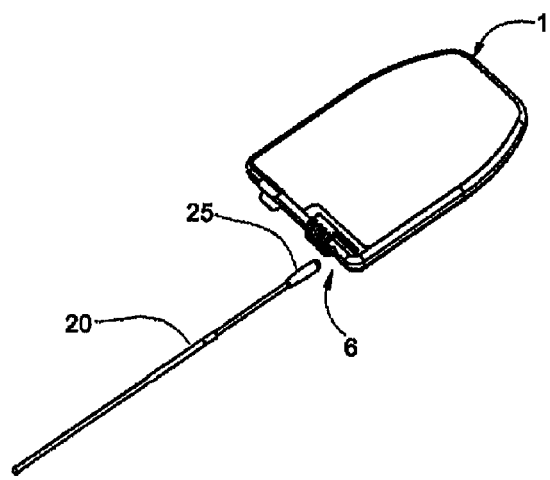
FIGS. 9A-E is a sequential view of the steps of a method in which a representative specimen collection device fitted with a disposable external sanitary skin is used to collect a specimen on a swab.
Figure 9B:
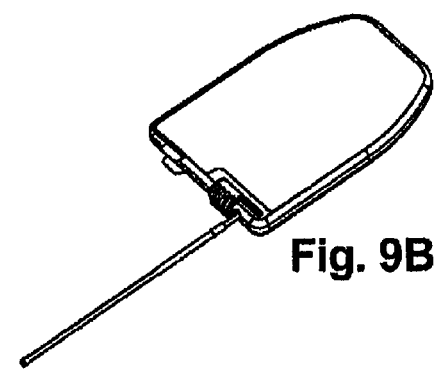
Figure 9E:
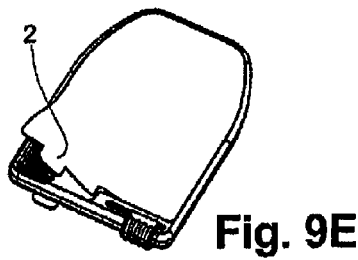
Figure 9C:
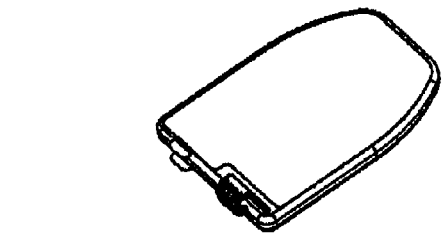
Figure 9D:
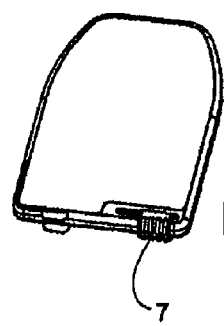

FIG. 8 shows a conceptual view of a more general form of the composite sample collection device (80) with disposable outer skin (81). Here the disposable outer layer material can be a quilted material, a composite of waterproof and absorbent layers, a diaper, a foil composite, and so forth. The material is knit or fused around the edges into a pouch holding the device, and is torn away at a frangible or pre-weakened tear point after the sample is collected. U.S. Pat. No. 4,279,344 describes a packaging laminate which is heat sealable and peelable suitable for this construction.

FIG. 9 is a pictorial representation of the essential features of the swab capture method, and shows a multistep process with steps A-E and a representative device (1) and swab (20). In FIGS. 9A and B, the swab (20) is oriented to the swab receiving orifice (6) of the device body (1) and the tip of the swab (25) is inserted into the device. In step C, the handle (22) is broken away and discarded. The locking closure (7) is then slid over the orifice (6) to irreversibly capture and seal the swab tip in the device, as shown in FIG. 9D. In step E, the disposable external skins, or "decals", are then peeled away (shown is the upper skin 2 peeling away), refreshing the external surfaces and removing any extraneous material inadvertently deposited when collecting the sample. The fresh external surfaces are used to label the specimen contents and patient identification, or optionally a label with that information can be applied to those surfaces.

FIG. 10 is a block diagram of these steps of the general method for swab capture. The steps are: collect a specimen on a swab; insert the swab tip into the collection device as designed for receiving the swab, and break off the swab handle; seal the swab in the device using a locking closure; remove the disposable skin or skins from the external surfaces of the collection device, taking care to avoid contaminating the freshly exposed surfaces. Optionally, an analysis may then be performed on the swab in the device without further exposure to the biohazardous sample.

Note that the order of the steps is not strictly followed if the swab handle is broken off and the device sealed after the external skins are removed, and it may be that handling the device in this way is more convenient. However, the preferred method is to capture the swab and seal the device before removing and discarding the external protective skins. As claimed, the invention is not limited by the order of these steps.

FIG. 11 is a block diagram of a more general method for specimen capture. The specimen is first collected and inserted in a suitable container, the container having been supplied with disposable external skin or skins; the container is then sealed; and the external skins or skins are removed and discarded.

Figure 12A:
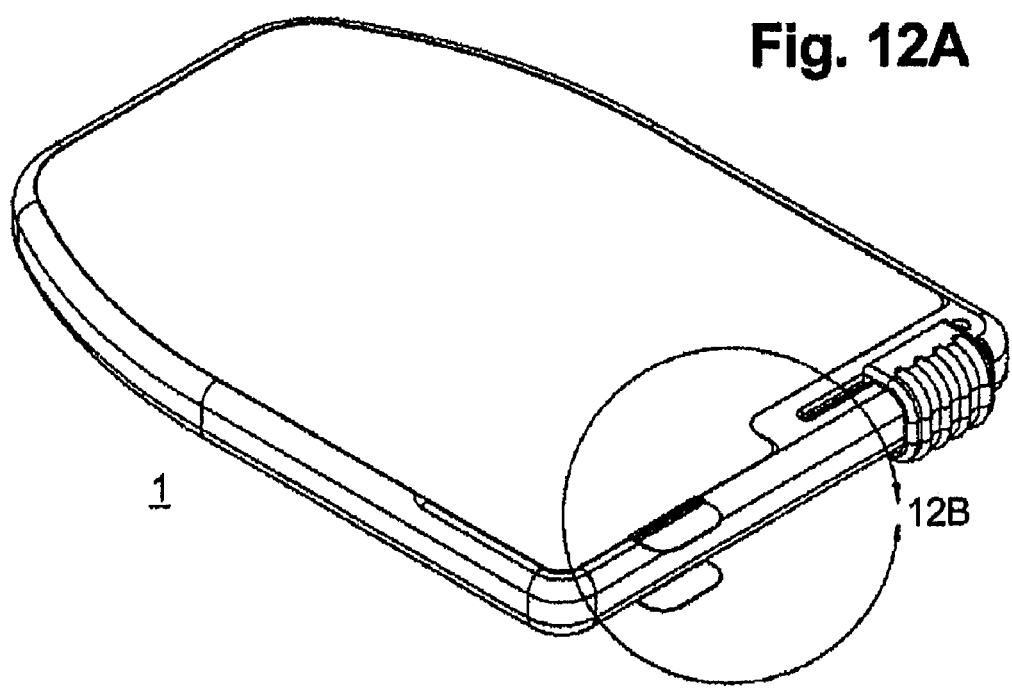
FIGS. 12A and B show a detail of a tab on the disposable external cover for use in removing the protective cover after the specimen is collected.
Figure 12B:
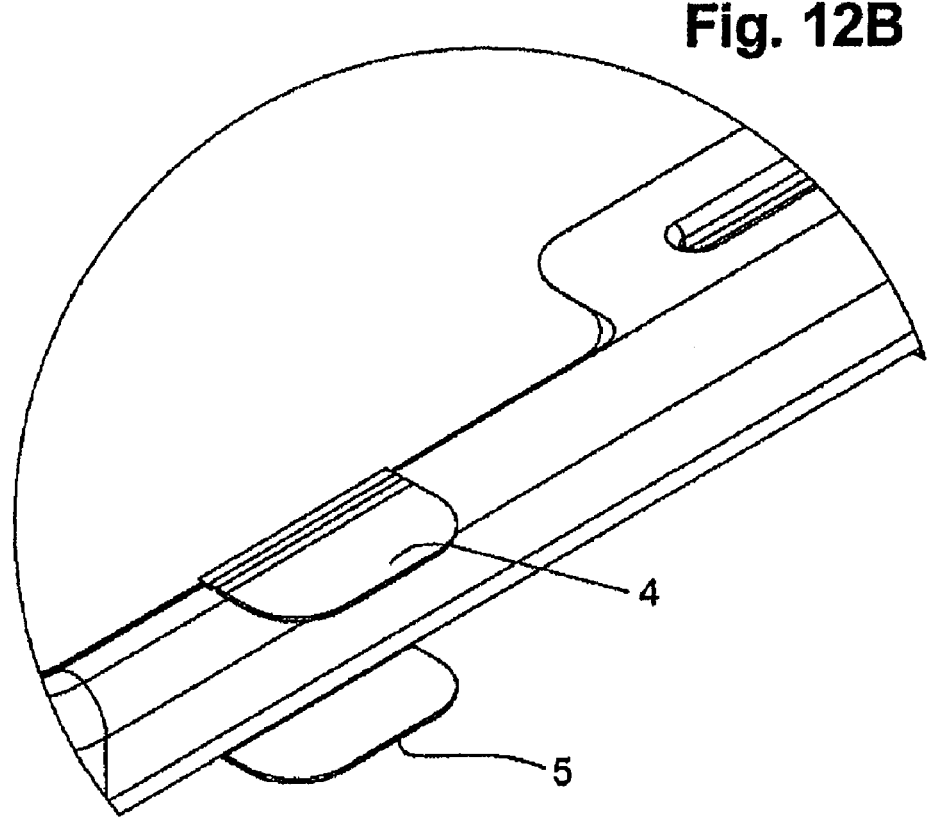

FIGS. 12A and 12B are overview and detail, respectively, of the tab members (4,5) used as a peelaway strip for removing the external skins of a representative device. As shown in detailed view 12B, the tabs are freestanding at the edges of the body of the device, and are easily grasped between finger and thumb. The entire protective film or pad is then readily peeled away.

Figure 13:
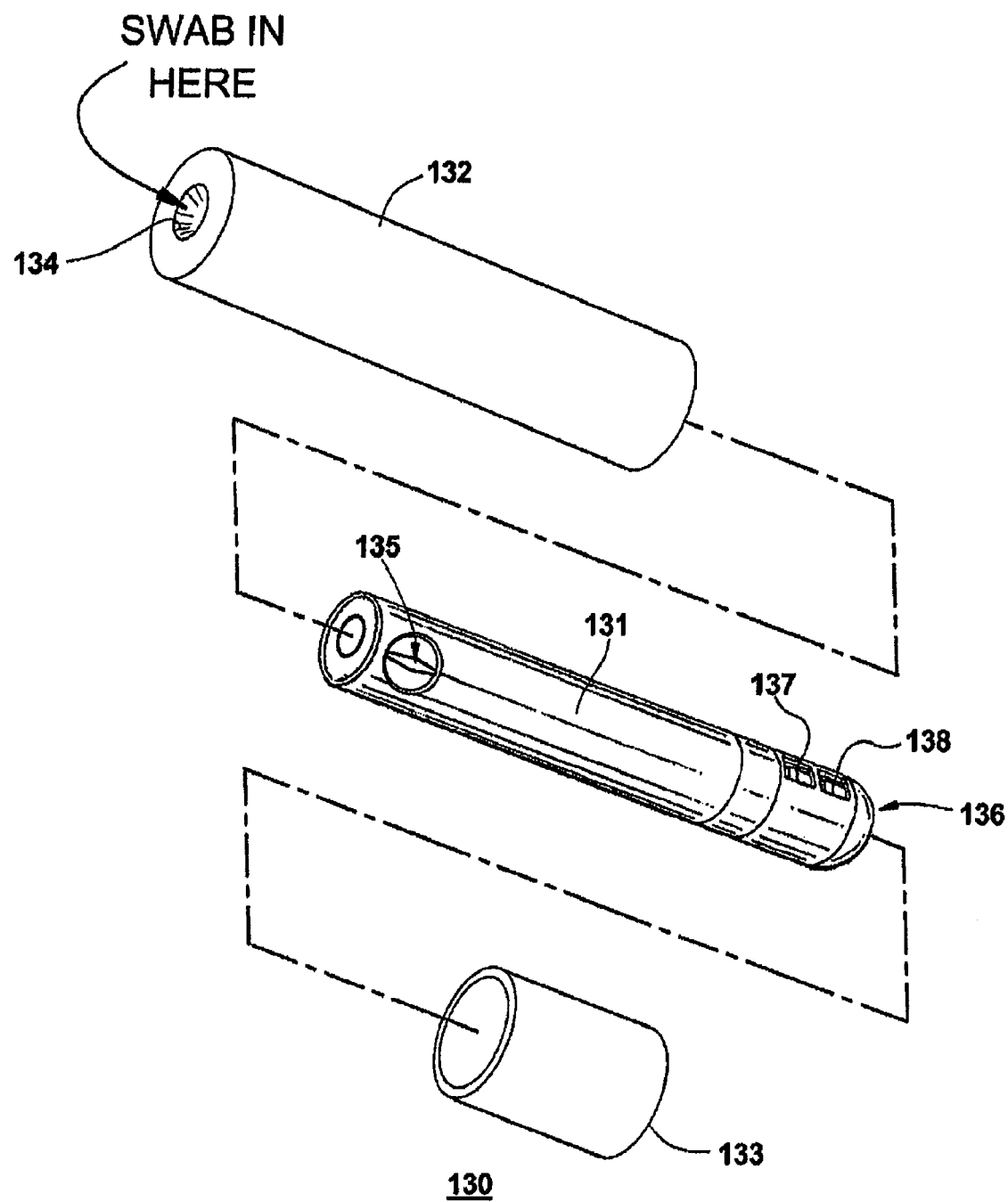
FIG. 13 is a second embodiment of a specimen collection device for a swab or tampon, and includes operator interface and real-time point-of-care data display that is hidden under the cap of a protective removable overlayer during specimen collection.

FIG. 13 is an alternate embodiment of a combination specimen collection container and sheath (130), showing an alternate form of the external protective skin and internal specimen collection device. Here the analytical device (131) shown is fitted with internal analytical works and a user interactive panel and display window.

In use, the body of the sample collection device 131 is encased in an outer sleeve member (132) and cap member (133). The outer sleeve member is supplied with an endwise swab receiving orifice (134) and internal swab receiving chamber for collecting the swab. A ball valve type closure is used to capture and seal the swab in the device and a knob is provided (135) for rotating the ball valve from open to closed. The control head 136 may also be rotated, and serves to power a spring-driven pressure source for the pumps, and to initiate the assay protocol. Assay status is shown in the leftmost window 137. Assay results are shown in the rightmost window 138.

After the sample is collected, the outside protective sleeve 132 is removed and the sample receiving chamber is closed with the ball valve 135. The cap can then be removed and the apparatus is generally free of external contamination. The sample entry end can be covered. The control head is then rotated and the assay commenced. In a few minutes, the assay result is read in the display window. Status and validity of the assay is displayed in the left panel. Optionally, the device can be inserted into a machine and the assay conducted by machine-aided power and control. The outer sleeve and cap are discarded as contaminated medical waste. At the completion of the assay, the device is also discarded along with its entrained specimen.

Note that the embodiment is illustrative of a general concept, and is not limited by its specificity. The outside protective sleeves are disposable external skins. The sleeves may be replaced by decals as described in FIG. 4, wherein the decals are adapted for a cylindrical body form. Similarly, the disposable protective overlayer may be as provided in FIGS. 5-8.

This device is also suitable for collection of tampons, which lack the handle characteristic of swabs. The tampon, however, must be inserted into the swab receiving orifice with tweezers or by other means and the orifice must be dimensioned appropriately. Tampons are useful sample collection devices, and their use is hereby taken within the scope of the invention described herein.

This device is conceived as part of a kit, the kit consisting of a sterile swab, the combination specimen collection device and sheath 130, and a tray. The tray optionally may also contain surgical gloves, instructions, and labeling aids.

Figure 14:
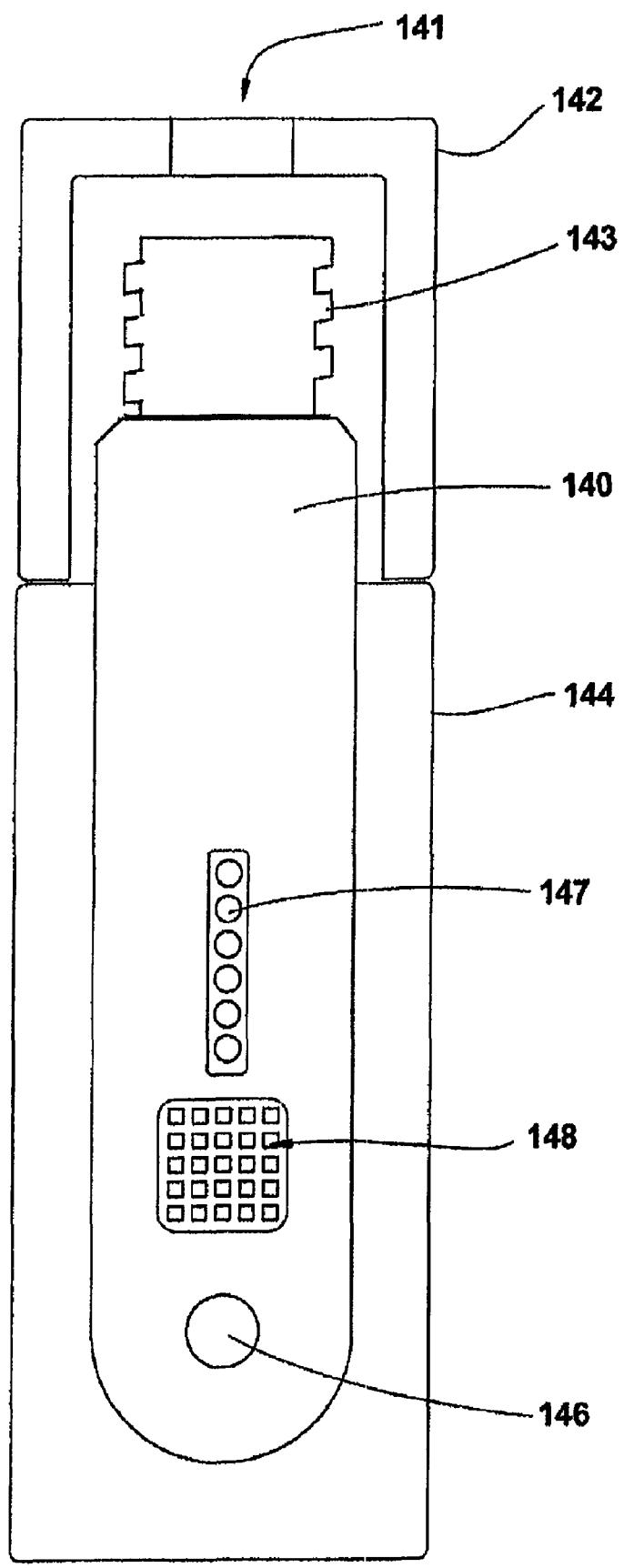
FIG. 14 is a section down the long axis of a third embodiment of a specimen collection device for a swab or tampon, and includes operator interface and real-time point-of-care data display that is hidden under a protective removable overlayer during specimen collection.

A variation of composite device 130 is shown in FIG. 14. Here the sample is inserted through orifice (141) in external disposable cap (142) into device (140), the body of which contains a sample receiving chamber with threaded neck (143). After the sample is deposited in the device, the cap 142 is immediately removed and a clean, sterile lid (not shown) is threaded onto the neck. The device body thus functions as bottle. Holding the assembly by the clean lid, the lower outside protective sheath (144) is then removed.

The external surfaces of the device are now clean and safely handled without gloves. Objectionable materials deposited on the outside sheath are discarded along with the disposable sheaths, which function as an external protective skin.

In this embodiment, the operator then presses the start button (146); the instrument cycles, its status continuously displayed in status bar 147, and the raw data is read from nucleic acid hybridization array 148. The machine is placed under a modified bar code reader or strip reader and the data is electronically displayed on the reader and transmitted as an electronic medical record to the patient's chart.

These various analytical features are not presently viewed as limitations of the present invention. The present invention relates to methods and devices for collecting specimens and for analyzing specimens in which a pre-formed disposable external skin is removed from the collection device or sample holder after the specimen is deposited in it.

Thus in FIG. 15, a swab collection container is shown with no analytical capabilities. The composite swab holder consists of an internal bottle and an external skin or sheath, so that after the swab is collected and sealed within the internal bottle, the external sheath is removed and the swab in its bottle, or other sealed vessel, is safely transported and handled with the assurance that any biohazardous external residues have been disposed of with the external sheath.

Swab collection container (150) is shown in FIG. 15A. Internal swab collection container (151) is shown in FIG. 15B. The two figures illustrate essentially a "before" and "after", wherein the device is supplied as shown in FIG. 15A without collected swab, and in FIG. 15B with collected swab. The steps involve capturing the swab and removal of the external skins, so that the product of the method is the slender, clean swab holder shown in FIG. 15B.

As supplied, the swab collection container 150 has a swab receiving port (153) formed of disposable funnel (154) and barbed lip (164) of the internal swab receiving channel (156), also termed herein an "internal hollow volume (156)". The temporary shipping cap (160) is first removed and the swab is inserted tip-down into the internal hollow volume (156). Note that the disposable funnel serves to protect the barbed rim (164) of the internal sheathed tube (157) from contamination with specimen residues. Following collection of the swab and placement within the inner tube, the sealing strip, or tear strip (168), is removed and the upper protective skin (155) is lifted up and away from the device, along with the disposable funnel 154, both of which are discarded. This exposes the uppermost bezeled rim 164 of the inner cylinder. Now, as shown in FIG. 15B, a sealing closure (165) with locking lip or flange (166) and plug (167) can be locked in place over the barbed bezel of the inner cylinder, and the outer lower protective sheath 159 is slid off the inner cylinder and discarded. The sealing closure is supplied separately. After these steps, the swab (152, 158) is now isolated within the internal hollow volume 156, separated from the external surfaces (169) by closure 165, and the external surfaces are as clean as supplied by the factory.

Note that the removal of the outer shells is a two part process. With a gloved hand, the contaminated outer shell is grasped and the upper shell is removed. A clean hand is then used to install the closure, and the upper part of the inner cylinder is held while the lower shell is removed. The final specimen container is now free of contamination and can be handled without gloves. To later gain access to the swab, fracture lines such as described in U.S. Pat. No. 6,516,947 may be formed in the internal cylinder, which can be formed generally as described in FIG. 1 of that publication. In that way, it is never necessary to touch the directly swab again. Alternatively, the closure of the device of FIG. 15 can be a threaded closure, and the internal cylinder may be formed with a mating threaded rim and sealing flange. Various combinations are anticipated.

If a patient were to collect the sample, we envisage that the patient will place the swab in the device and return it, outer shell intact, to a healthcare professional or laboratory technician. The technician will then complete the steps of removing the upper shell, inserting and sealing the cap, and then removing the lower shell, taking care to avoid contaminating the external surfaces of the inner cylinder during the process.

Between steps of the process, the device 150 may be stood on its base, which can be formed with a foot as would be useful for stability.

A kit for this process may contain, in a tray, the device 150, a swab 20, and a closure, along with any instructions and labeling.

It will be appreciated by persons skilled in the art that numerous variations, combinations of elements, and/or modifications may be made to the invention as shown in the specific embodiments without departing from the spirit or scope of the invention as broadly described. The present embodiments are, therefore, to be considered in all respects as illustrative and not restrictive.

EXAMPLES

Example 1

A swab is provided in a sterile packet, the shaft of the swab being formed with a notch separating the handle from the sampling tip. The swab is rubbed in the gingiva separating the teeth from the gums of a child and inserted into a collection device of the invention. The swab handle is bent vigorously so that it breaks at the notch, releasing the swab tip with specimen into the device. The swab insertion channel is then covered with a sliding closure that rides in tracks in the housing, and sealed irreversibly, the sliding closure having a ratcheted underside which mates and locks over a locking tooth or spur on the body of the device. The professional then removes a protective external skin from the device, taking care not to contaminate the freshly exposed surfaces, and hands the device to an aide for processing.

Example 2

A swab is provided in a sterile envelope, the shaft of the swab being formed of a material suitable for cutting with a blade. The patient is asked to provide a self-collected specimen of the vaginal mucosa and is given instructions. The patient collects the sample and inserts the soft tip of the swab into the sample collection device that was provided. The patient hands the device to a health professional, who takes it with gloved hands. The health professional closes the cover of the device, cutting free the swab handle and discarding it, and then removes the disposable external skins on the device, taking care not to contaminate the freshly exposed surfaces. After removing the skins, the health professional inserts the device into a semi-automated analytical apparatus and completes the assay. The result is read and the device with sample is then discarded. The analytical apparatus is equipped with networking capability so as to transmit identifying and "smart" electronic data as an electronic medical record to a database on a server.

What is claimed is:

1. A method for collecting a test sample, the method comprising:
    a) providing a sample collection device comprising:
        i) a body having an external surface, the external surface defining at least one swab receiving orifice with internal hollow volume for receiving a swab, the swab receiving orifice compatible with a sealable closure that may be sealably closed over the swab receiving orifice; and
        ii) a removable disposable external skin layer or shell covering at least a portion of the external surface of the body; and
    b) providing instructions comprising
        i) inserting the swab into the swab receiving orifice and sealably closing the sealable closure over the swab receiving orifice;
        ii) handling the sample collection device by contacting the external disposable skin layer or shell prior to or during insertion of the swab into the swab receiving orifice and closure of the sealable closure over the swab receiving orifice;
        iii) removing the removable disposable external skin layer or shell from the body with a clean hand after insertion of the swab into the swab receiving orifice and closure of the sealable closure over the swab receiving orifice, thereby exposing the at least a portion of the external surface of the body; and
        iv) handling the exposed external surface with clean hands, wherein the method reduces or eliminates contamination with a biohazard during sample collection or analysis.

2. The method of claim 1, wherein the sample collection device further comprises a second removable external skin layer or shell covering a second portion of the external surface, and the method further comprises removing the second removable external skin layer or shell with a clean hand.

3. The method of claim 1, wherein the swab comprises a handle with frangible neck and an absorbent tip for collecting the test sample.

4. The method of claim 3, wherein the method further comprises inserting the absorbant tip into the swab receiving orifice and breaking off the handle at the frangible neck.

5. The method of claim 1, wherein the swab is a tampon.

6. The method of claim 1, wherein the test sample is a biosample.

* * * * *